(12) United States Patent
Visconti

(10) Patent No.: US 8,002,732 B2
(45) Date of Patent: Aug. 23, 2011

(54) MEDICAL SUCTION AND IRRIGATION DEVICE

(75) Inventor: Peter L. Visconti, Gurnee, IL (US)

(73) Assignee: Allegiance Corporation, McGaw Park, IL (US)

( * ) Notice: Subject to any disclaimer, the term of this patent is extended or adjusted under 35 U.S.C. 154(b) by 424 days.

(21) Appl. No.: 11/526,871

(22) Filed: Sep. 26, 2006

(65) Prior Publication Data
US 2007/0106204 A1    May 10, 2007

Related U.S. Application Data

(60) Provisional application No. 60/720,787, filed on Sep. 27, 2005.

(51) Int. Cl.
*A61M 1/00* (2006.01)
*A61M 25/00* (2006.01)

(52) U.S. Cl. ........... 604/28; 604/27; 604/33; 604/35; 604/523

(58) Field of Classification Search ............ 604/27, 604/28, 35, 33, 500, 523
See application file for complete search history.

(56) References Cited

U.S. PATENT DOCUMENTS

| | | | |
|---|---|---|---|
| 3,603,347 A | | 9/1971 | Paolini |
| 4,526,573 A | * | 7/1985 | Lester et al. .................. 604/33 |
| 5,120,305 A | * | 6/1992 | Boehringer et al. ........... 604/35 |
| 5,496,314 A | | 3/1996 | Eggers |
| 5,522,796 A | * | 6/1996 | Dorsey, III ................. 604/118 |
| 5,722,949 A | | 3/1998 | Sanese |
| 5,782,834 A | | 7/1998 | Lucey |
| 5,807,313 A | * | 9/1998 | Delk et al. .................... 604/35 |
| 6,213,970 B1 | * | 4/2001 | Nelson et al. ................ 604/35 |
| 6,652,488 B1 | * | 11/2003 | Cover et al. ............... 604/118 |
| 2001/0011162 A1 | * | 8/2001 | Epstein ...................... 604/30 |
| 2004/0158203 A1 | * | 8/2004 | Cover et al. ............... 604/118 |
| 2007/0106204 A1 | * | 5/2007 | Fedenia et al. ............... 604/28 |

* cited by examiner

*Primary Examiner* — Nicholas D Lucchesi
*Assistant Examiner* — Ian K Holloway
(74) *Attorney, Agent, or Firm* — Arent Fox LLP

(57) ABSTRACT

Embodiments of the invention provide a suction evacuation system, or smoke evacuation system, for incorporation into hand-held surgical devices. In particular, the system according to embodiments of the invention can be used in hand-held surgical suction-irrigation devices that may also include electrical systems which deliver energy to effect cutting, ablation and coagulation effects at the surgical site. Embodiments of the invention provide a smoke evacuation system that can be incorporated into a hand-held surgical device wherein the smoke evacuation system is structurally and functionally integrated with the suction control system of the device.

44 Claims, 19 Drawing Sheets

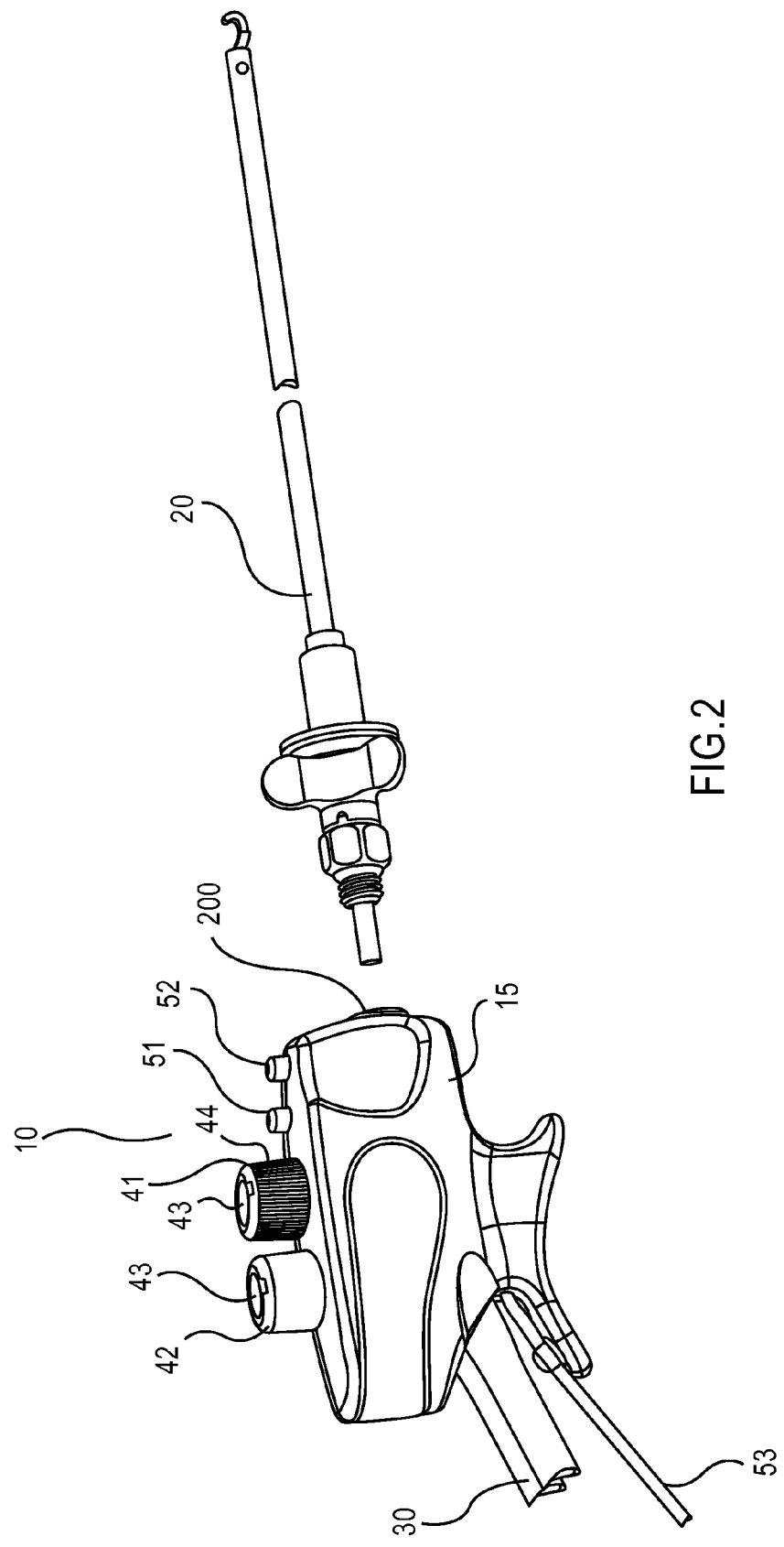

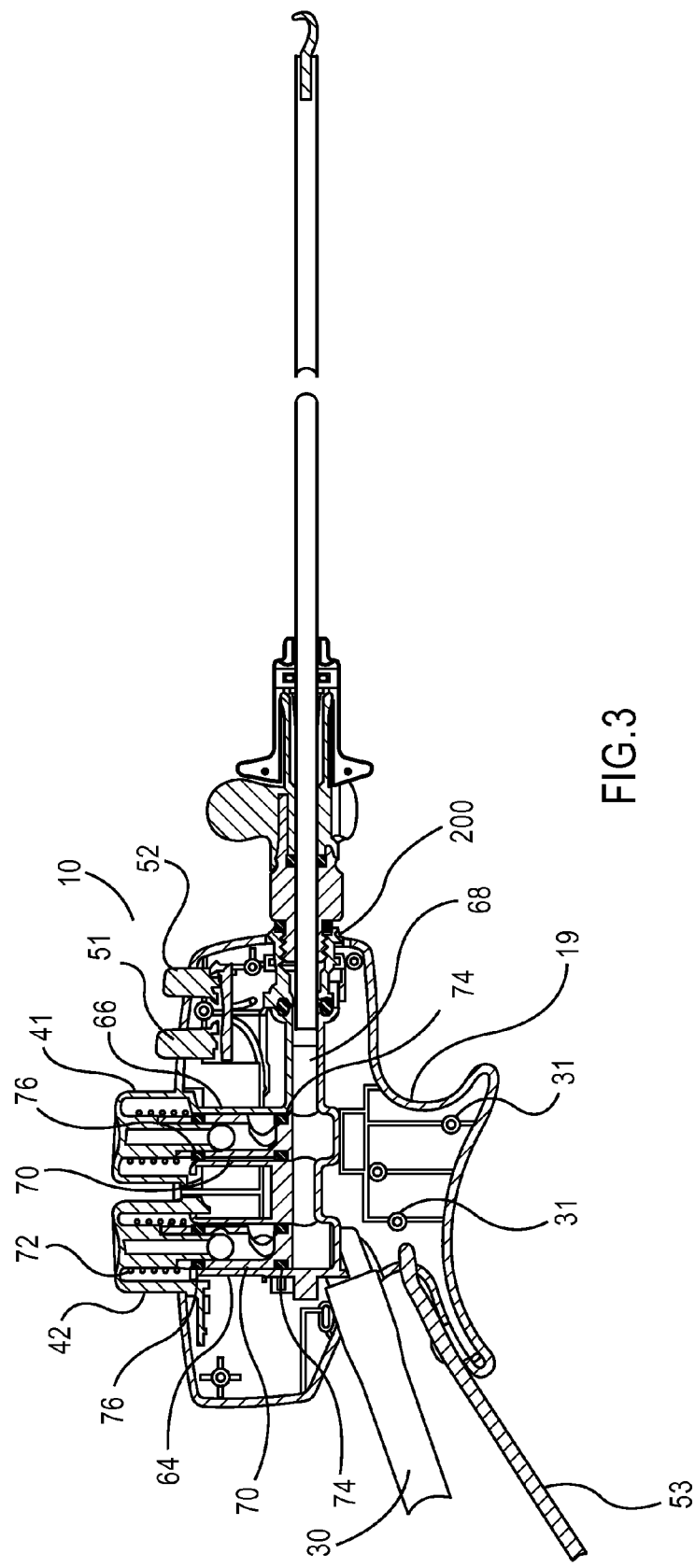

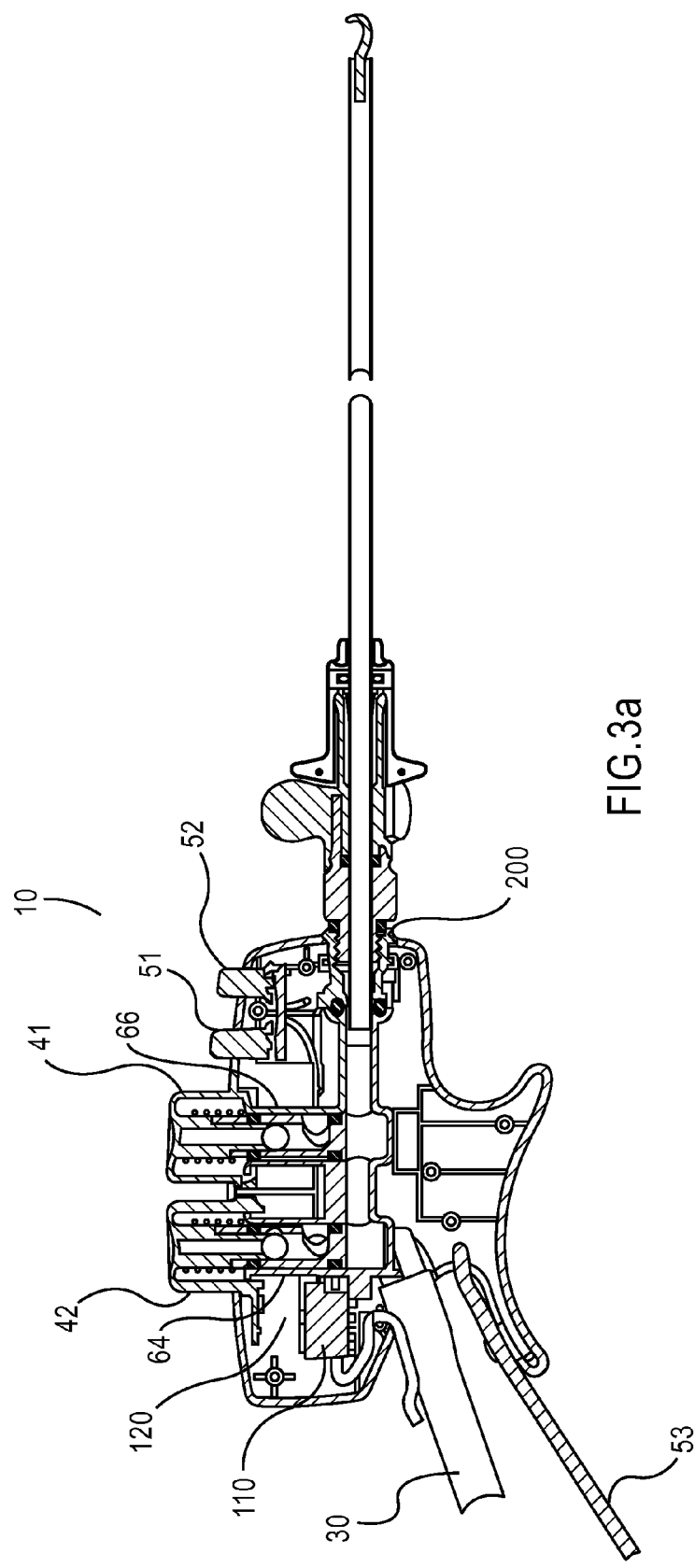

Irrigation not Activated

Irrigation Activated

Right side of Manifold

Suction / Smoke Evac Side

Suction not Activated

Smoke Evacuation Activated

Suction Activated

MEDICAL SUCTION AND IRRIGATION DEVICE

CROSS REFERENCE TO RELATED APPLICATIONS

This application claims the benefit of U.S. Provisional Application No. 60/720,787, filed Sep. 27, 2005, under 35 U.S.C. §119(e). The entire disclosure of that provisional application is incorporated by reference herein.

DESCRIPTION OF THE INVENTION

1. Field of the Invention

The invention relates generally to medical devices, such as, for example, medical devices that provide multiple functions during a medical procedure. More particularly, embodiments of the invention relate to hand-held medical devices providing suction and irrigation capabilities for use with an underlying medical diagnostic or treatment instrument.

2. Background of the Invention

A wide variety of hand-held medical devices are known in the medical field. Certain invasive surgical procedures utilize electrical-sourced cutting, ablating, coagulation, and/or cauterizing instruments. Within the particular treatment location, such as, for example, within an internal cavity of the patient's body undergoing treatment, such procedures can generate steam, vapors, and smoke from heated or burnt tissue. When this occurs, visualization of the surgical site can become obscured, leading to potential dangerous conditions for the patient.

In situations where steam, vapors, smoke, or body fluids cause visualization problems, known medical procedures often required the use of an additional suction instrument provided at the treatment location in order manage proper visualization. A variety of suction evacuation systems are known in the surgical field. Of particular interest is the capability for hand-held devices to include both the instrument with which to perform the procedure, and suction-evacuation systems that remove vapors and smoke produced by certain procedures. Although there have been suction-evacuation system designs in the surgical field, there remains the need for improvement in their structure, operation and functionality, as well as ease of manufacture and assembly, including aspects of cost and efficiency. Accordingly, there is a need in the medical field, particularly the surgical field, for hand-held devices (e.g., suction-irrigation devices) having features that provide multiple surgical functions in an easily manufactured and assembled design that facilitates the ease of operation.

SUMMARY OF THE INVENTION

Accordingly, the present invention is directed to improved hand-held medical devices, and related methods of use that obviate one or more of the limitations and disadvantages of the prior art medical devices.

One embodiment of the invention is directed to a medical device including a housing and an attachment structure along a front end of the housing configured for coupling to a medical instrument. At least one of a suction port or an irrigation port at a proximal end of the housing is configured for connection to a source of suction or irrigation respectively and a conduit provides a fluid flow path from the at least one port at the proximal end of the housing to a distal port leading to the medical instrument. At least one valve is configured to move within the fluid flow path to selectively actuate suction or irrigation, and wherein the valve is configured to rotate to permit a first level of suction or irrigation and is configured to axially displace to permit a second, higher level of suction or irrigation.

In various embodiments, the device may include one or more of the following additional features: wherein the valve is configured for axial displacement regardless of a rotational orientation of the valve; wherein the at least one valve comprises a piston located within a housing chamber, the piston movable between a first position blocking fluid flow along the fluid flow path and a second position allowing fluid flow along the fluid flow path; wherein the piston is engaged with an actuation button and maintained in the first position through a compression spring positioned between the housing chamber and the actuation button; wherein the conduit defines a lumen along a distal portion thereof, the piston includes at least one aperture, and the piston is in the second position when the aperture is moved to at least partially align the aperture with the lumen; wherein the piston is engaged with an actuation button and maintained in the first position through a compression spring positioned between the housing chamber and the actuation button; wherein depressing the actuation button compresses the spring and displaces the piston within the housing chamber to at least partially align the aperture with the lumen; wherein the valve is configured to provide an incremental adjustment of a magnitude of applied irrigation or suction; wherein the incremental adjustment is effectuated by a degree to which the aperture is aligned with the lumen; wherein axial displacement of the piston within the housing chamber controls a degree to which the aperture is aligned with the lumen; further comprising a spring tab located on the housing and a series of spaced slots connected to the piston, and wherein the spring tab releasably engages each slot to maintain a particular alignment between the aperture and lumen upon movement of the piston; wherein the valve is configured to provide an incremental adjustment of a magnitude of applied irrigation or suction; wherein a suction control button extends from the housing, and wherein axial displacement of the suction control button provides the second level of suction, and rotation of the suction control button provides the first level of suction; wherein the suction control button includes a knurled exterior surface; further comprising a spring tab located on the housing and a series of spaced slots along an exterior surface of the suction control button, and wherein the spring tab is configured to consecutively releasably engage each slot upon rotation of the control button to engage a particular slot with the tab; wherein the at least one suction port or an irrigation port is a suction port and an irrigation port provided at the proximal end of the housing, the suction port configured for connection to a source of suction, and the irrigation port configured for connection to a source of irrigation; a first fluid passageway provides a first fluid flow path from the suction port to the distal port, a second fluid passageway provides a second fluid flow path from the irrigation port to the distal port, the at least one valve comprises a first valve configured to move within the first fluid flow path to selectively actuate suction, wherein the first valve is configured to rotate to permit a first level of suction and is configured to axially displace to permit a second, higher level of suction; wherein the at least one valve comprises a second valve configured to move within the second fluid flow path to selectively actuate irrigation, wherein the second valve is configured to axially displace to permit actuation of irrigation; wherein the valves are configured for axial displacement regardless of a rotational orientation of the valves; wherein the first and second valves have pistons with substantially identical configurations; wherein the at least one valve comprises a piston defining a cylinder having a lower distally directed aperture located along an external surface of the cylinder, the piston further including an upper, transverse aperture extending completely through an upper portion of the cylinder; wherein each cylinder includes a lower "o"-ring seal and an upper "o"-ring seal circumscribing an external surface of the cylinder; wherein an exterior surface of the housing chamber includes a ramp that extends between a first limit and a second limit, and the actuation button includes an inward protrusion that engages the ramp such that rotating the actuation button between the limits causes at least partial alignment between the aperture and the lumen; and wherein the medical device includes electric conductors providing electric current configured to connect to a medical instrument and wherein the first level of suction comprises smoke evacuation.

Another embodiment of the invention is directed to a method for operating a medical device to perform a medical procedure. The method includes providing a medical device including a medical instrument connected to a front end of a handpiece, a handpiece housing, and at least one of a suction port or an irrigation port at a proximal end of the housing configured for connection to a source of suction or irrigation respectively. A conduit provides a fluid flow path from the at least one port at the proximal end of the housing to a distal port leading to the medical instrument. At least one valve is configured to move within the fluid flow path to selectively actuate suction or irrigation, and wherein the valve is configured to rotate to permit a first level of suction or irrigation and is configured to axially displace to permit a second, higher level of suction or irrigation. The method further comprises connecting at least one of the suction port and the irrigation port to a source of suction or irrigation, positioning the medical instrument proximate a treatment site, and actuating either irrigation or suction by controlling movement of the valve.

In various embodiments, the method may include one or more of the following additional features: further comprising incrementally adjusting the magnitude of applied irrigation or suction; wherein a suction control button extends from the housing of the medical device, and the method further comprises axially displacing the suction control button to provide suction; further comprising rotating the suction control button to provide the first level of suction; further comprising rotating the suction control button prior to axially displacing the suction control button; wherein an irrigation control button extends from the housing of the medical device, and the method further comprises axially displacing the irrigation control button to provide irrigation; further comprising rotating the irrigation control button to adjust a magnitude of applied irrigation; further comprising cauterizing tissue with the medical instrument prior to rotating the suction control button; wherein providing the medical device further comprises providing a suction port and an irrigation port provided at the proximal end of the housing, the suction port configured for connection to a source of suction, and the irrigation port configured for connection to a source of irrigation; providing a first fluid passageway providing a first fluid flow path from the suction port to the distal port, a second fluid passageway providing a second fluid flow path from the irrigation port to the distal port, the at least one valve comprising a first valve configured to move within the first fluid flow path to selectively actuate suction, wherein the first valve is configured to rotate to permit a first level of suction and is configured to axially displace to permit a second, higher level of suction; the method further comprising connecting at least one of the suction and irrigation ports to a source of suction or irrigation; and actuating both irrigation and suction by controlling movement of the first and second valves; wherein the medical device includes structure that releasably engages the valve and the method further comprises maintaining an intermediate level of suction or irrigation by maintaining a particular rotational or axial position of the valve.

Another embodiment is directed to a medical device comprising, a housing, an attachment structure along a front end of the housing configured for coupling a medical instrument, and a suction port and an irrigation port provided at the proximal end of the housing, configured for connection to a source of suction and irrigation respectively. A first fluid passageway provides a first fluid flow path from the suction port at the proximal end of the housing, extending through a suction piston chamber, and out a lumen defined by a distal conduit leading to the medical instrument. A second fluid passageway provides a second fluid flow path from the irrigation port at the proximal end of the housing, extending through an irrigation piston chamber, and out the lumen defined by a distal conduit. An identical movable piston is provided within each of the suction piston chamber and the irrigation piston chamber and the piston in the suction piston chamber is configured to rotate and axially translate to provide suction to the medical instrument.

In various embodiments, the device may include one or more of the following additional features: wherein the piston in the suction piston chamber is configured for axial displacement regardless of a rotational orientation of the piston; wherein each piston defines a cylinder having a lower distally directed aperture located along an external surface of the cylinder, the piston further including an upper, transverse aperture extending completely through an upper portion of the cylinder; wherein the lower aperture is oriented in substantially perpendicular relation to the axis defined by the upper, transverse aperture; wherein each cylinder includes a lower "o"-ring seal and an upper "o"-ring seal circumscribing an external surface of the cylinder; wherein the lower aperture and the upper aperture are both located between the lower and upper "o"-ring seals along the cylinder of the piston; wherein each piston is engaged with an actuation button and maintained in a first position through a compression spring positioned between the piston chamber and the actuation button; wherein depressing an actuation button compresses the spring and displaces the piston within the piston chamber to at least partially align an aperture in the piston with the first or second fluid passageway; further comprising a spring tab located on the housing and a series of spaced slots along an exterior surface of the actuation button that controls suction, and wherein the spring tab is configured to consecutively releasably engage each slot upon rotation of the control button to engage a particular slot with the tab; wherein an exterior surface of the suction piston chamber includes a ramp that extends between a first limit and a second limit, and the actuation button includes an inward protrusion that engages the ramp such that rotating the actuation button between the limits causes at least partial alignment an aperture in the piston with the first fluid passageway; and wherein the medical device includes electric conductors providing electric current configured to connect to a medical instrument Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is an angled side view of a medical device handpiece having an instrument spaced from a front end thereof, according to an embodiment of the present disclosure.

FIG. 3 is a cross-sectional view of one embodiment of a medical device, according to an embodiment of the present disclosure.

FIG. 3a is a cross-sectional view of another embodiment of a medical device, according to an embodiment of the present disclosure.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts. For purposes of this disclosure, "distal" refers to the end further from the device operator during use and "proximal" refers to the end closer to the device operator during use.

Figure 1:
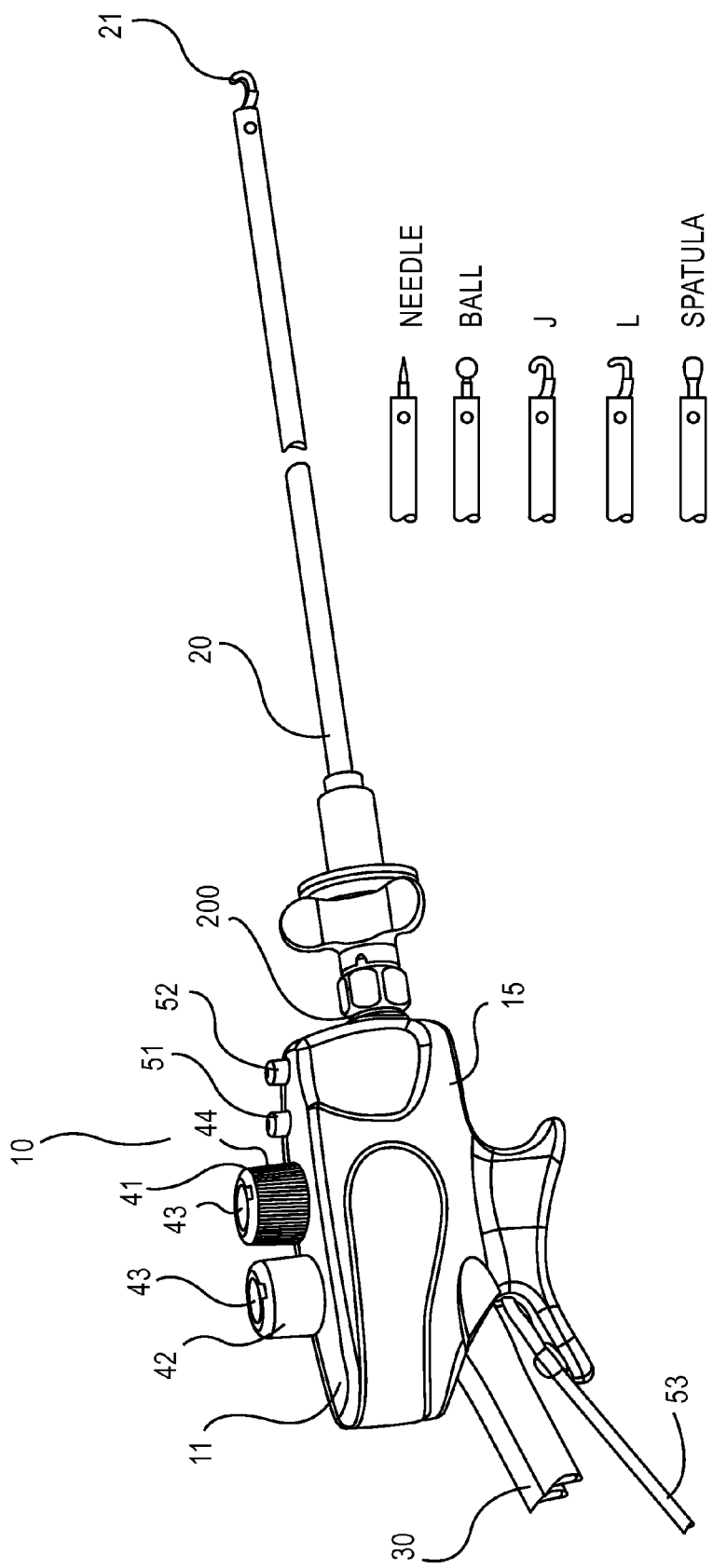
FIG. 1 is an angled side view of a medical device handpiece having an instrument connected at a front end thereof and illustrating a number of alternative instruments, according to an embodiment of the present disclosure.

Referring to FIG. 1, one embodiment of a medical device 10, according to the invention, includes a handpiece 15 onto which a medical instrument 20 (shown as a probe), can be removably coupled or uncoupled (see FIG. 2), and into which tubing 30 (e.g., suction and irrigation tubing) can be attached. While medical instrument 20 is depicted as a probe (or alternatively as an electrosurgical probe), instrument 20 may comprise a basket, a grasper, a snare, any other retrieval or grasping mechanism, a tissue cutting instrument, any electrocautery device, a forceps, or any other mechanism for performing an operation in a body that may be suitable for a medical diagnostic or treatment procedure. FIG. 1 depicts instrument 20 as a surgical probe having an end-effector comprised of a curved hook 21 for manipulating a patient's tissue during surgery. FIG. 1 also illustrates a number of alternative end-effectors having various shapes, such as, for example, a needle, a ball shaped implement, a "J" hook, an "L" hook, and a spatula-shaped implement. The preceding list in not intended to be exclusive or otherwise limiting the invention, and alternative examples are contemplated.

In this disclosure, handpiece 15 is primarily described as a handpiece for use in a medical suction and irrigation device. The handpiece 15 may connect to a source of irrigation fluid, such as a saline bag (not shown). The irrigation fluid may be supplied to the handpiece through tubing 30 via a pump unit (not shown). The pump unit may include, for example, a motor, impeller, power source, and other conventional parts known in the art. The handpiece 15 may also connect to a source of suction, such as a conventional vacuum source available in a hospital room setting. Suction would be supplied through tubing 30. Handpiece 15 further may connect to a source of electric current via wires 53, for supplying electrocautery to a patient via a conductive end-effector. It is to be understood, however, that some or all of the aspects of the handpiece 15 could be used with other types of medical devices.

The handpiece 15 is defined by a housing 11. The particular shape ergonomic features, and grasping enhancements exhibited by handpiece 15 are expressly described in co-pending U.S. application Ser. No. 11/526,872 filed on Sep. 26, 2006, (the same date as the present application), the entire contents of which are hereby incorporated by reference.

As seen in FIG. 1, the housing 11 extends to an instrument attachment structure 200 within housing 11 for removably coupling a medical instrument 20 thereon. Incorporated by reference application Ser. No. 11/526,872 also includes a description of structure 200, its coupling to instrument 20, and various features of instrument 20, including its proximal collar. Reference is made to that application for that disclosure.

In the illustrated embodiment, the handpiece 15 of the medical device includes the components of a suction control button 41 and an irrigation control button 42. The top surface of control buttons 41 and 42 may each include a concave depression 43 for facilitating reception of an operator's fingertips for actuation thereof. The control buttons 41 and 42 may have certain characteristics to visually distinguish one button from the other. For example, as seen in FIG. 1, suction control button 41 may have a knurled pattern 44 along an exterior side surface, whereas irrigation control button 42 has a smooth exterior side surface. Other distinguishing characteristics are contemplated, such as a difference in color, for example. As will be described in more detail below, the knurled exterior of suction control button 41 facilitates gripping and rotation thereof by an operator.

In addition, the handpiece 15 of the medical device may include additional operative mechanisms such as electrical control buttons 51 and 52 for operative coupling to electrical wiring 53, to permit connection to an additional power source (not shown), for example. In one embodiment, wiring 53 may connect to a source of electric current and buttons 51 and 52 are actuated to selectively supply current to medical instrument 20. The supply of current may be used to assist in cutting and/or cauterizing tissue. For example, operation of buttons 51, 52 may cause electric current to be supplied to the tip of instrument 20. As further examples, operation of buttons 41, 42 may respectively cause suction to be applied through instrument 20 and a supply of irrigation fluid through instrument 20. Moreover, as will be described in more detail below, the medical device may include the capability to selectively activate smoke evacuation rather than a full-blown suction operation. For example, the suction control button 41 may be activated to vary the amount of suction applied to the treatment site. Furthermore, in embodiments, the medical device provides an operator with the capability to alter the magnitude of the applied smoke evacuation between various low, various intermediate, and high levels of applied smoke evacuation.

Figure 4:
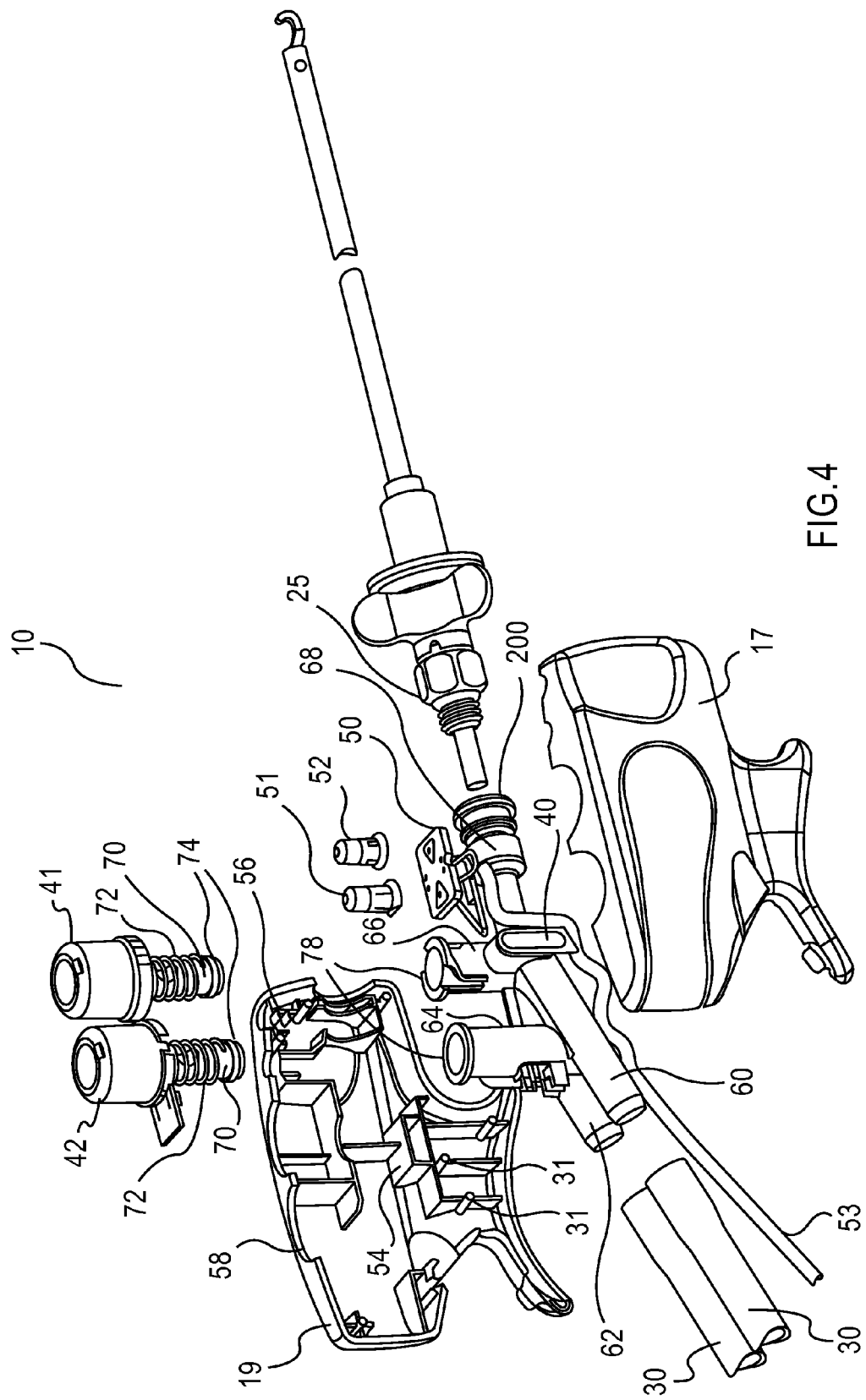
FIG. 4 is a disassembled perspective view of a medical device handpiece and an instrument, according to an embodiment of the present disclosure.

FIGS. 3 and 4 depict cross-sectional and disassembled perspective views respectively of the same medical device 10 and handpiece 15. FIG. 4 depicts an exploded view of the internal and external structure of a medical suction and irrigation device. In FIG. 4, a first (right) housing half 17 is separated from a second (left) housing half 19. The first and second halves 17 and 19 may each be formed through a molding process such that they are configured to receive the internal components therebetween. During manufacture and assembly, the first and second halves 17,19 may enclose the internal device components upon a mating engagement therebetween. For example, the interior of the first half 17 may include male pin mating protrusions configured for receipt within female pin apertures 31 formed on the interior of the second half 19.

As seen in FIG. 4, the internal components of the handpiece 15 may include the internal electric wiring 53, a manifold assembly 40, and a conducting platform 50 for providing a transmission path for an electric circuit from wiring 53 to the control buttons 51 and 52. Each half 17, 19 may include internal structure, such as preformed protrusions 54 defining separate chambers within the inside of each housing half, for receiving a particular component of the manifold assembly 40 and/or the wiring structure 53. For example, the second half 19 may include protrusions arranged to form a slot 56 configured to snugly receive the conducting platform 50 therein. In this configuration, the buttons 51, 52 are positioned to engage the platform 50 in order to complete an electric circuit thereby providing electric current via wire 53 to the instrument 20. In addition, the handpiece 15 may include a semi-circle configuration 58 for snugly receiving an exterior portion of the manifold assembly 40.

The manifold assembly 40 includes structure for routing suction and irrigation flow-paths in a predetermined configuration to a distal end of the handpiece where the pathways connect to an appropriate conduit within a distal medical instrument. More particularly, the manifold assembly may comprise a proximal suction port 60 configured for connection to a portion of tubing 30 connected to a vacuum source (or other suction generation), a proximal irrigation port 62 configured for connection to a portion of tubing 30 connected to an irrigation source, an irrigation piston valve housing chamber 64, a suction piston valve housing chamber 66, and a distal manifold fluid conduit 68. The terminal portion of the distal manifold fluid conduit 68 comprises an engagement portion 200 having internal threads configured to removably engage a medical instrument, such as instrument 20 via engagement with external threads 25, for example. As will be described in more detail below, the manifold assembly 40 is arranged such that proximal suction port 60 and proximal irrigation port 62 are capable of fluid communication with the distal manifold fluid conduit 68 (the internal lumen of which is depicted in cross-section in FIGS. 3 and 3a).

With reference to FIGS. 3 and 4, the medical device handpiece 15 includes a suction control button 41 and an irrigation control button 42 as previously described. Each button 41 and 42 is engaged with a valve piston 70 and a compression spring 72. Each piston 70 has a generally cylindrical outer shape and includes a lower "o"-ring seal 74 and an upper "o"-ring seal 76 that circumscribes the exterior cylindrical shape of the piston. As seen in FIG. 3, each piston 70 is configured for receipt within one of the piston valve housing chambers 64 and 66. The compression springs 72 are sized to encircle their respective pistons 70 and to encircle an internal post within each of the buttons 41 and 42. As depicted in FIG. 3, a top end of the compression spring 72 contacts an upper internal surface of the control button 41 or 42, while a bottom end of the compression spring 72 contacts a top lip 78 (see FIG. 4) on each of the piston valve housing chambers 64 and 66. Accordingly, upon assembly in the configuration of FIG. 3, the compression springs 72 maintain the control buttons 41 and 42 (and therefore each of the pistons 70) in an upward position. Moreover, upon compression of springs 72 via actuation of control buttons 41 and 42, the pistons 70 are capable of displacement within chambers 64 and 66 and into the flow path between the proximal suction port 60 or the proximal irrigation port 62 and the distal manifold fluid conduit 68.

Figure 4A:
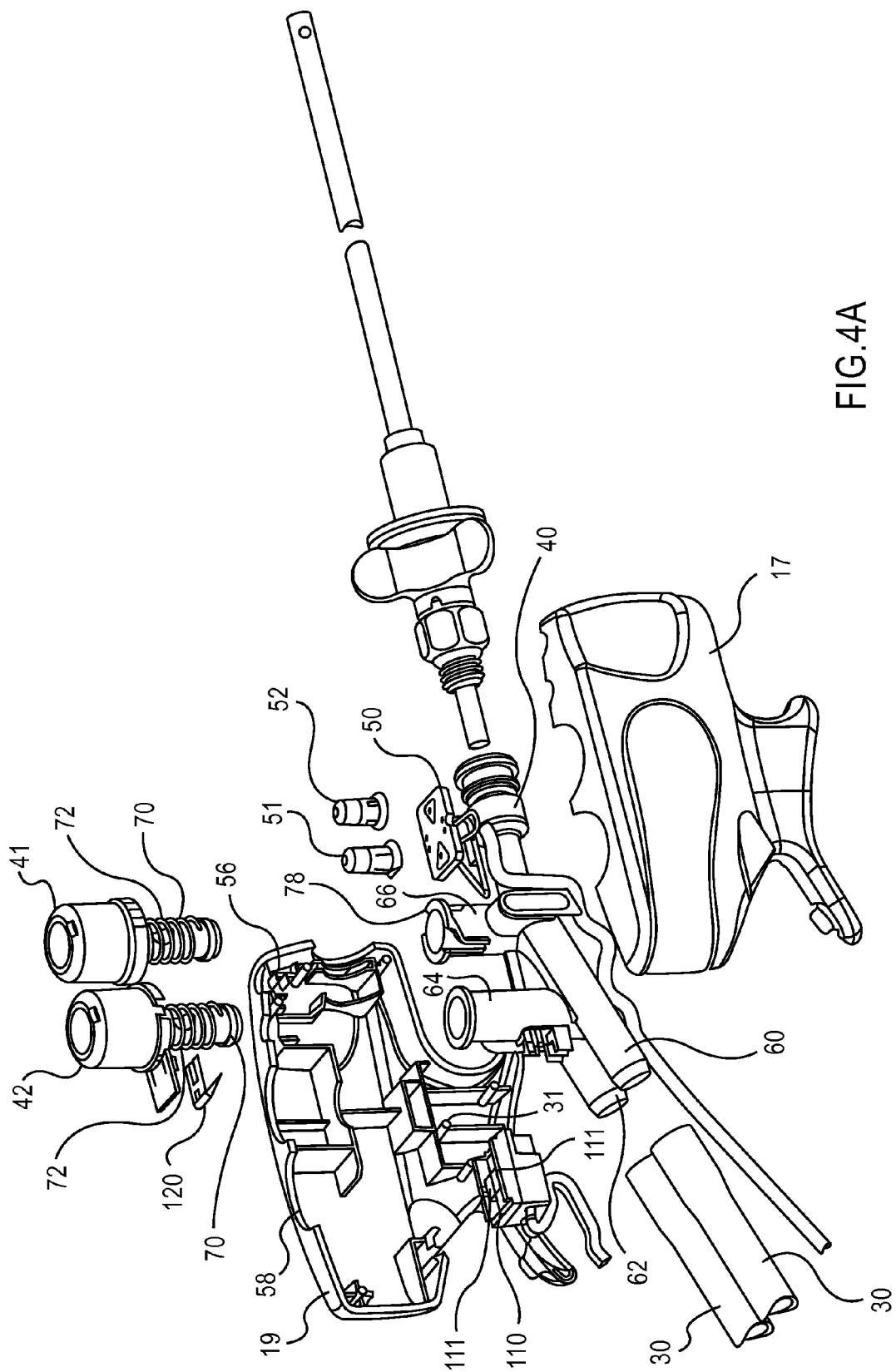
FIG. 4a is a disassembled perspective view of another medical device handpiece and an instrument, according to an embodiment of the present disclosure.

All of FIGS. 1-4a show the structure of actuation control buttons 41 and 42. In the illustration of FIGS. 3 and 4, there is no depiction of any power source components or electric connections for selectively actuating a electric device to assist in providing irrigation. Accordingly, the configurations of FIGS. 3 and 4 may provide irrigation from a fluid source (e.g., a saline bag) positioned to promote fluid flow under the force of gravity via an IV pole, for example. FIGS. 3a and 4a depict a medical device 10 differing from the arrangement of medical device 10 in FIGS. 3 and 4 only by virtue of irrigation source power component 110. As illustrated in FIGS. 3a and 4a, power component 110 may present spaced apart electrically conductive contacts 111 on a top surface thereof. The power source component 110 may be connected to a source of forced irrigation (e.g. an electric motor, pump, and/or impeller). Upon depressing irrigation control button 42 of FIGS. 3a and 4a, the conductive contact tangs 120 can contact the exposed spaced apart contacts 111 on the top surface of component 110, thereby closing an open circuit and providing power to a fluid pump, for example.

Figure 17:
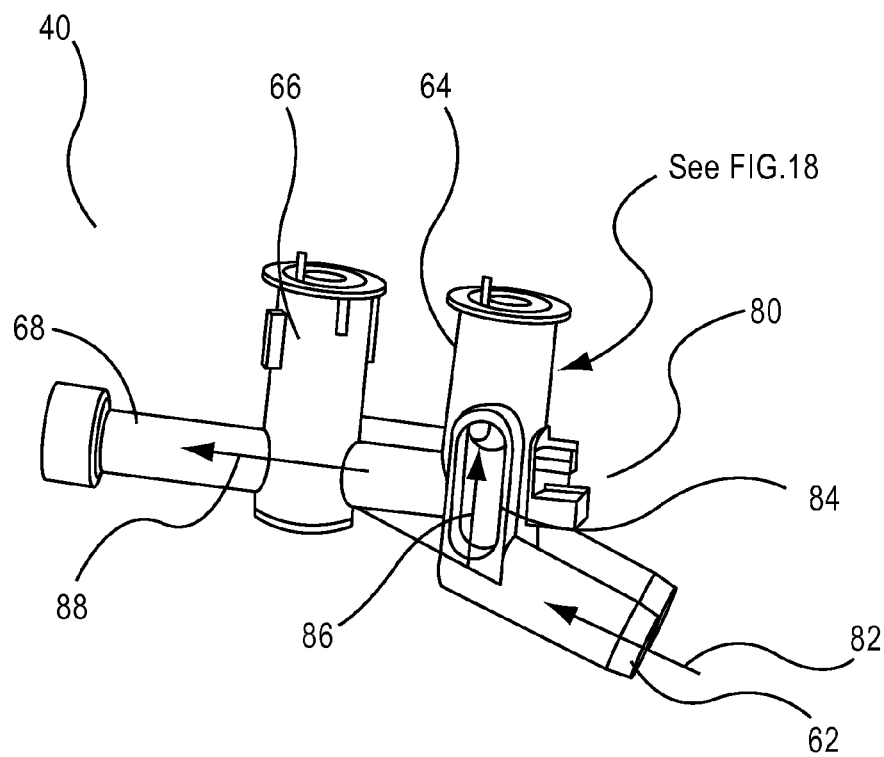
FIG. 17 is a perspective view of a manifold component of a medical device, according to an embodiment of the present disclosure.

Exemplary fluid flow paths for the medical device will now be described. An exemplary configuration and flow path for manifold assembly 40, and the interaction of pistons 70 therewith, is illustrated in FIGS. 17-24B. FIG. 17 is a perspective view of a manifold assembly 40 illustrating an irrigation fluid flow path 80. As shown, fluid from an irrigation source, depicted by arrow 82, enters proximal irrigation port 62. The flow path 80 continues to a lateral transfer conduit 84 where fluid is directed along an upward path (see flow path arrow 86) and then extends laterally along a medial path into the irrigation piston valve housing chamber 64.

Both the irrigation piston valve housing chamber 64 and the suction piston valve housing chamber 66 lead to, and are in direct fluid communication with, the distal manifold fluid conduit 68, as seen in FIGS. 3, 3a, 19, 20, 23, 24A, and 24B. Therefore, without considering the interaction of piston 70 within chamber 64, irrigation fluid would follow a flow path 80 from the proximal irrigation port 62, into the lateral transfer conduit 84, into the chamber 64, and out the distal manifold fluid conduit 68 (as depicted by arrow 88) to a treatment location (via an internal lumen of a connected instrument, for example).

Figure 21:
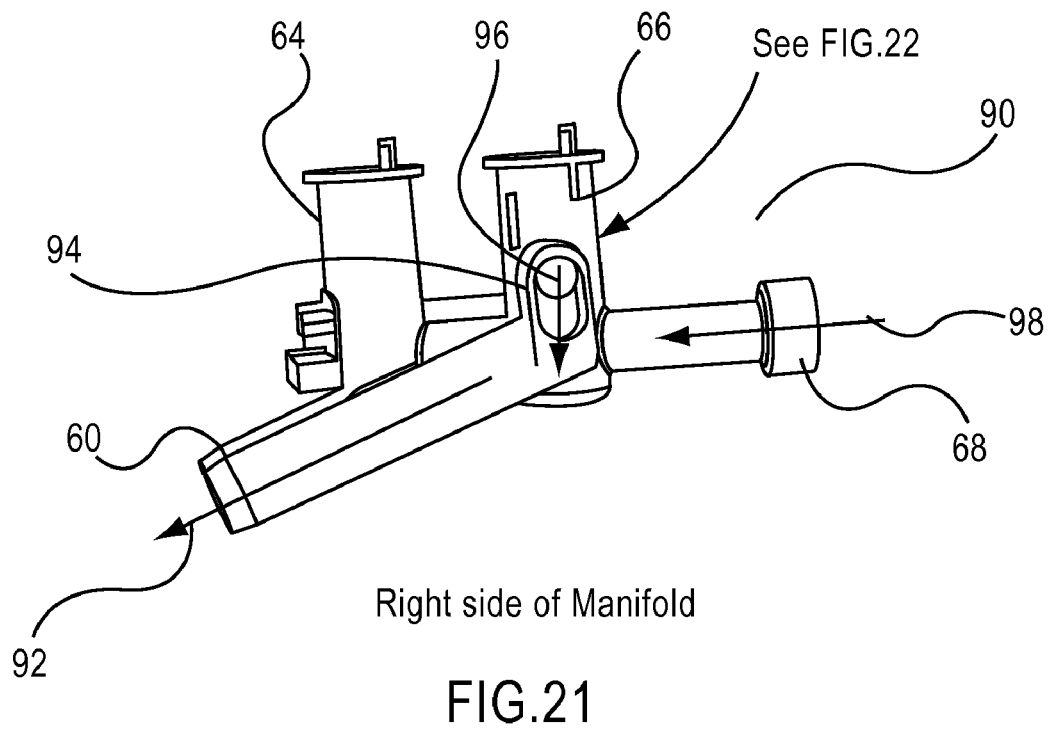
FIG. 21 is a perspective view of a manifold component of a medical device, according to an embodiment of the present disclosure.
Figure 22:
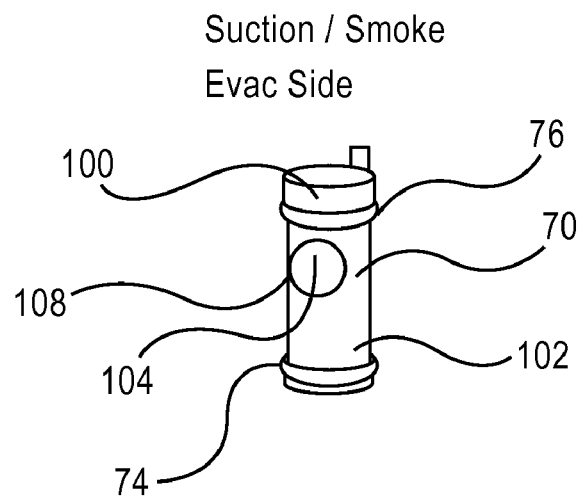
FIG. 22 is a perspective view of a fluid valve component, according to an embodiment of the present disclosure.
Figure 23:
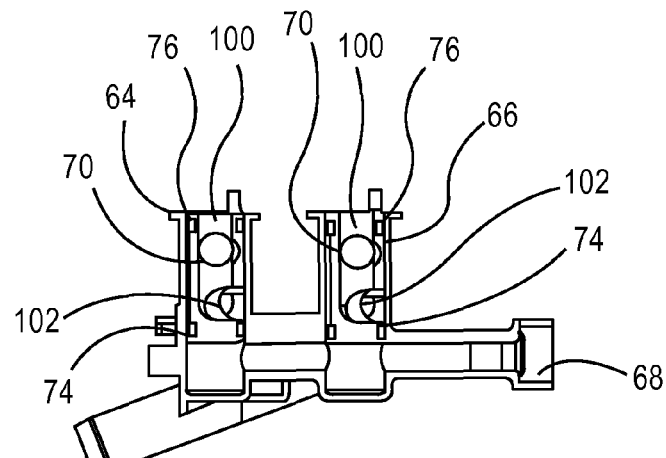
FIG. 23 is a partial side cross-sectional view of a manifold component of a medical device depicting a first configuration, according to an embodiment of the present disclosure.
Figure 24A:
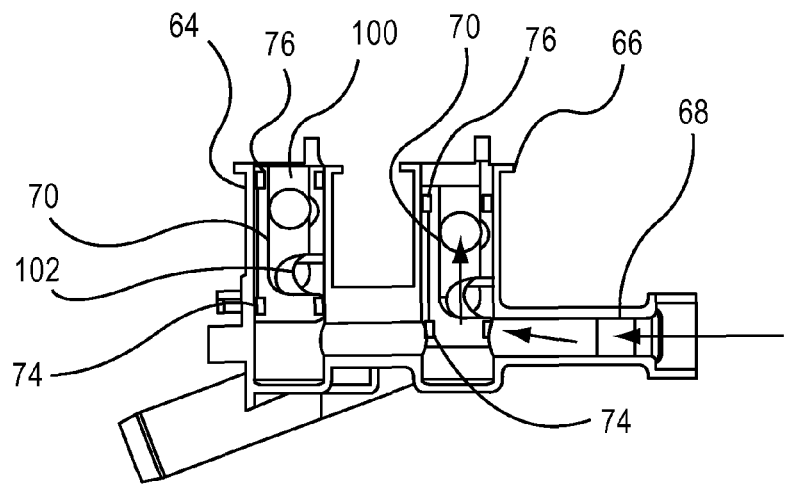
FIG. 24A is a partial side cross-sectional view of a manifold component of a medical device depicting a second configuration, according to an embodiment of the present disclosure.
Figure 24B:
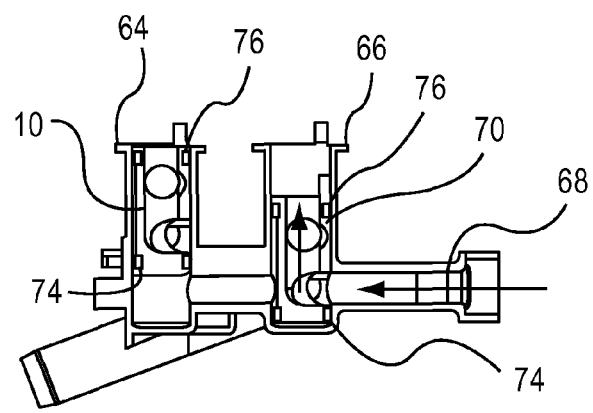
FIG. 24B is a partial side cross-sectional view of a manifold component of a medical device depicting a third configuration, according to an embodiment of the present disclosure.

FIG. 21 is a perspective view of a manifold assembly 40 illustrating a suction conduit flow path 90. As shown, a proximal suction force is generated and connected to the proximal suction conduit 60, depicted by arrow 92. During application of suction, the flow path 90 begins at the distal manifold fluid conduit 68 as seen in FIGS. 21, 23, 24A, and 24B. The flow path continues into the suction piston valve housing chamber 66 and then the path extends sideways, outward laterally, into the lateral transfer conduit 94. The flow path then continues along a downward path (along the path of arrow 96) and out of the proximal suction port 60, and into tubing 30 toward the source of suction. As noted above, the suction piston valve housing chamber 66 leads to, and is in direct fluid communication with, the distal manifold fluid conduit 68, as seen in FIGS. 23, 24A, and 24B. Therefore, without considering the interaction of piston 70 within chamber 66, applied suction would act on fluid to follow a flow path 90 from the distal manifold fluid conduit 68 (as depicted by arrow 98), into the chamber 66, into the lateral transfer conduit 94, laterally outward and then along the downward path 96, out of the proximal suction port 60, and into tubing 30 toward the source of suction.

With reference to the description of flow paths 80 and 90 above, and as seen in FIGS. 17 and 21, the distal manifold fluid conduit 68 is centrally located between the laterally spaced location for suction port 60 and irrigation port 62. The arrangement of each side of manifold assembly 40 is similar in that the assembly 40 provides a flow path that starts at a proximal and laterally spaced port (i.e. at either suction port 60 or irrigation port 62) and follows a distal path directed medially (via either lateral transfer conduit 84 or lateral transfer conduit 94) into the irrigation piston valve housing chamber 64 or the suction piston valve housing chamber 66. As will be described in more detail below, this arrangement of manifold 40 allows for the use of a universal design for piston 70 in each chamber 64 and 66, thereby promoting cost-efficiency and ease of assembly.

Figure 18:
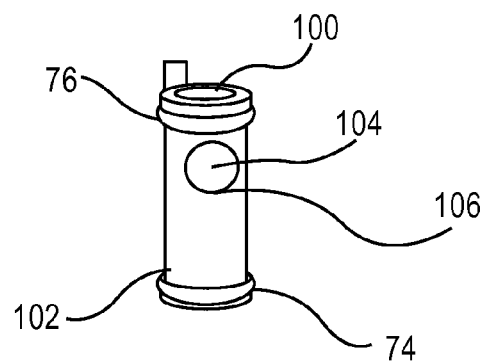
FIG. 18 is a perspective view of a fluid valve component, according to an embodiment of the present disclosure.

The configuration of pistons 70 and their relative position within each of chambers 64 and 66 modifies the resulting flow path within the manifold assembly 40 in order to allow an operator to selectively control the application of suction (including suction for smoke evacuation) and irrigation. With reference to FIGS. 3, 3a, 5B, 18-20, and 22-24B, each piston 70 has an generally cylindrical outer shape and includes a lower "o"-ring seal 74 and an upper "o"-ring seal 76. As seen in FIG. 18, for example, piston 70 comprises a cylinder having a hollow internal lumen 100 therein. The cylinder of piston 70 defines a lower, distally directed aperture 102. Aperture 102 is located along an external surface of the cylinder of piston 70 and is directed radially outwardly, perpendicular to the longitudinal axis of the cylinder of piston 70. Aperture 102 exposes the internal lumen 100 of the piston 70.

Piston 70 further defines an upper, transverse aperture 104 extending completely through an upper portion of the cylinder forming piston 70. Accordingly, aperture 104 defines two openings, first opening 106 and second opening 108 (see FIG. 5B), in the body of piston 70, which are located on opposing sides of piston 70 and in alignment with one another. As seen in FIGS. 18 and 5B, the first opening 106, the second opening 108, and aperture 102 are arranged such that the aperture 102 is oriented in substantially perpendicular relation (i.e. offset by about 90 degrees) to the transverse axis shared by the first and second openings 106 and 108.

As seen in FIGS. 3, 3a, 5B, 18-20, and 22-24B, the distally directed aperture 102 is located just above the lower "o"-ring seal 74. Openings 106 and 108 defined by transverse aperture 104 are located just below the upper "o"-ring seal 76. Having described one exemplary structural configuration for manifold assembly 40 and piston 70, the relative position of piston 70 within each of chambers 64 and 66 and the resulting effect on the irrigation and suction flow paths will now be described.

Figure 19:
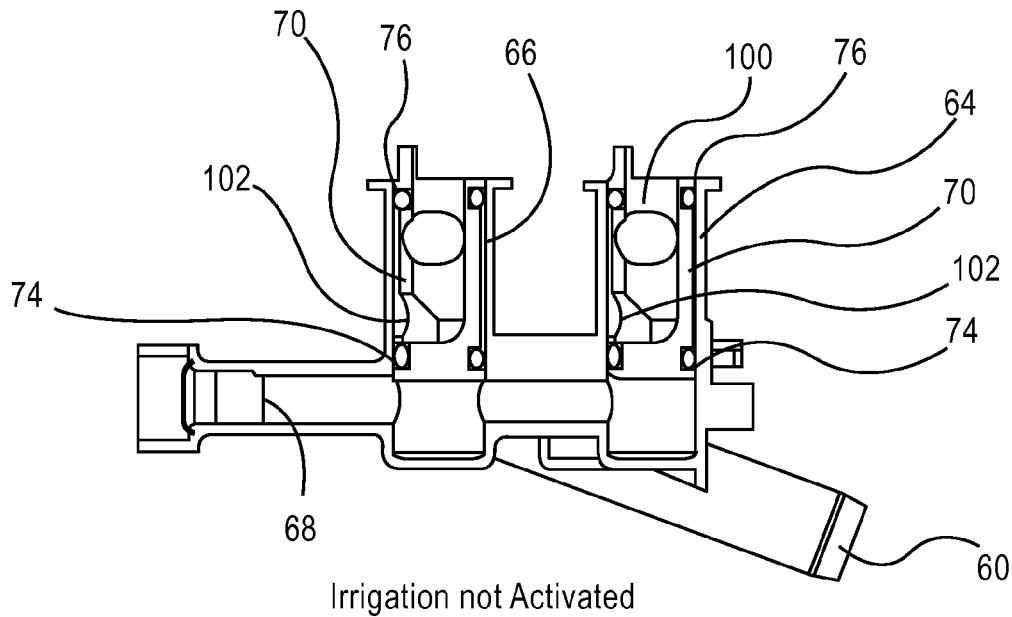
FIG. 19 is a partial side cross-sectional view of a manifold component of a medical device depicting a first configuration, according to an embodiment of the present disclosure.

With reference to FIGS. 5B and 17-20, a mechanism of irrigation actuation will be described. As described above, by virtue of compression spring 72, depressing either of control buttons 41 and 42 will result in displacement of the corresponding piston 70 within the corresponding chamber 64 and 66 and into the flow path of the distal manifold fluid conduit 68. FIG. 19 depicts a partial side cross-sectional view of a manifold assembly 40 illustrating the distal manifold fluid conduit 68 and a cross-sectional view of pistons 70 located in a first resting position within each of the irrigation piston valve housing chamber 64 and the suction piston valve housing chamber 66. As seen in FIG. 19, in the first, resting position, the misalignment of the distally directed aperture 102 and the distal manifold fluid conduit 68 prevents fluid communication. In addition, the lower "o"-ring seal 74 within chamber 64 blocks fluid communication along irrigation flow path 80 between the lateral transfer conduit 84 and the distal manifold fluid conduit 68. Irrigation fluid can enter the internal lumen 100 of the piston 70 (from the lateral transfer conduit 84), however, the vertical resting position of piston 70 and the seal provided by the lower "o"-ring seal 74 effectively blocks fluid communication along irrigation flow path 80 into the distal manifold fluid conduit 68. Fluid enters internal lumen 100 of piston 70 from the lateral transfer conduit 84 via aperture 104 and, more particularly, via first opening 106.

Figure 20:
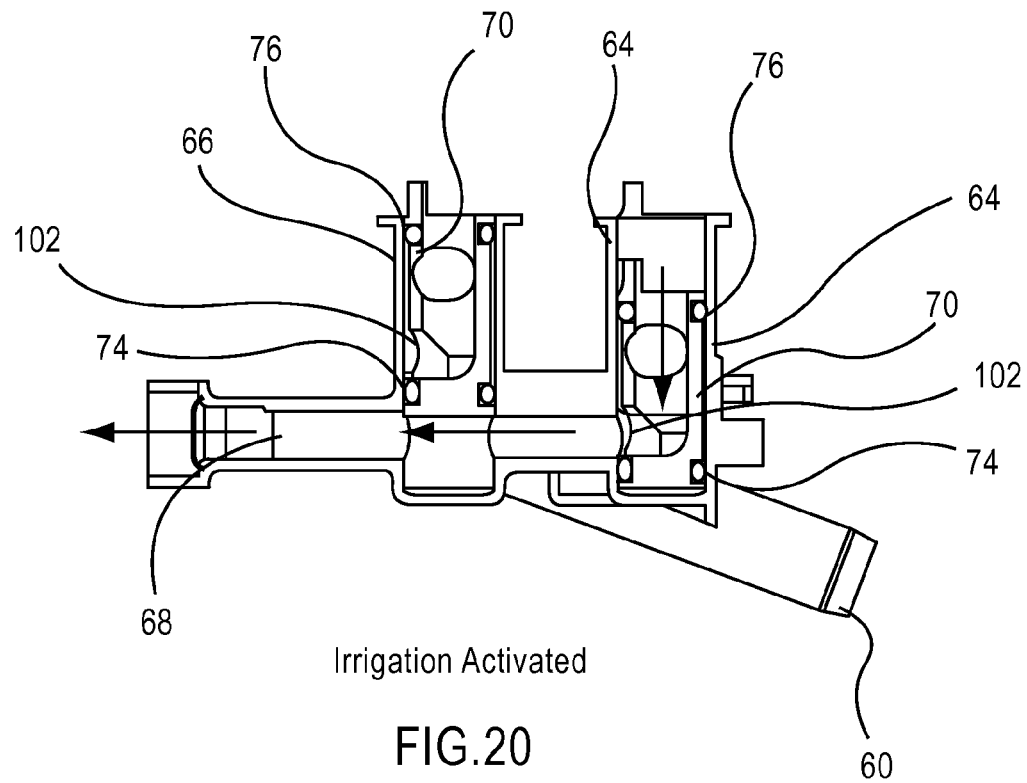
FIG. 20 is a partial side cross-sectional view of a manifold component of a medical device depicting a second configuration, according to an embodiment of the present disclosure.

As seen in FIG. 20, upon depressing irrigation control button 42 against the force of spring 72, the piston 70 within the irrigation piston valve housing chamber 64 is displaced downwardly, thereby unblocking the flow path between lateral transfer conduit 84, chamber 64, and the distal manifold conduit 68. As shown, irrigation fluid previously stopped within the internal lumen 100 of piston 70 can now exit lumen 100 via the distally directed aperture 102 and into the distal manifold conduit 68. Upon subsequent release of the irrigation control button 42, the piston 70 moves (under the force of compression spring 72) from the depressed, second position of FIG. 20 back to the first, resting position of FIG. 19.

The displacement of piston 70 within the suction piston valve housing chamber 66 effectuates suction, including smoke evacuation. For example, FIG. 23 shows pistons 70 located in a first resting position within each of the irrigation piston valve housing chamber 64 and the suction piston valve housing chamber 66. As seen in FIG. 23, in the first, resting position, the misalignment of the distally directed aperture 102 and the distal manifold fluid conduit 68 prevents fluid communication. In addition, the lower "o"-ring seal 74 within chamber 66 blocks fluid communication along suction flow path 90 between the distal manifold fluid conduit 68 and lateral transfer conduit 94.

Suction is applied at the proximal suction port 60 and continues into the internal lumen 100 of the piston 70 (from the lateral transfer conduit 94), however, the vertical resting position of piston 70 (where the distally directed aperture 102 is misaligned with the distal manifold fluid conduit 68) prevents fluid communication. In addition, the seal provided by the lower "o"-ring seal 74 effectively blocks fluid communication along suction flow path 90 into the distal manifold fluid conduit 68. Suction force acts within the internal lumen 100 of piston 70 from the lateral transfer conduit 94 via aperture 104 and, more particularly, via second opening 108.

As noted above, and as can be understood from FIG. 5B, for example, the resulting arrangement of each side of manifold assembly 40 is similar in that the assembly 40 provides a flow path that starts at a proximal and laterally spaced port (i.e. at either suction port 60 or irrigation port 62) and follows a distal path. The path, in both cases enters a similarly constructed lateral transfer conduit 84, 94, and then is similarly directed into the irrigation piston valve housing chamber 64 or the suction piston valve housing chamber 66. As a result, the suction control button 41 and the irrigation control button 42 can function using an identical design for piston 70 in each chamber 64 and 66, thereby reducing cost, promoting efficiency, and facilitating ease of assembly.

As seen in FIG. 24A, by slightly depressing suction control button 41 against the force of spring 72, the piston 70 within the suction piston valve housing chamber 66 is displaced downwardly, thereby unblocking the suction flow path 90 between lateral transfer conduit 94, chamber 66, and the distal manifold conduit 68. As shown, piston 70 is displaced by at least a distance sufficient for the lower "o"-ring seal 74 to enter the flow path of the distal manifold conduit 68, thereby allowing a lower magnitude of suction than would result from full displacement (see, e.g., FIG. 24B). Accordingly, an operator can adjust the magnitude of suction by varying the size of the opening created along the suction flow path 90. This size can be selectively controlled and adjusted as a function of the displacement distance piston 70 is displaced within chamber 66.

As seen in FIGS. 24A and 24B, suction force previously blocked within the internal lumen 100 of piston 70 (via the lower "o"-ring seal 74) can now act through lumen 100 via the distally directed aperture 102 and pull vacuum within the distal manifold conduit 68. Upon subsequent release of the suction control button 41, the piston 70 moves (under the force of compression spring 72) from the slightly depressed second position (FIG. 24A), or from the third, more fully depressed position (FIG. 24B) back to the first, resting position of FIG. 23.

Figure 5A:
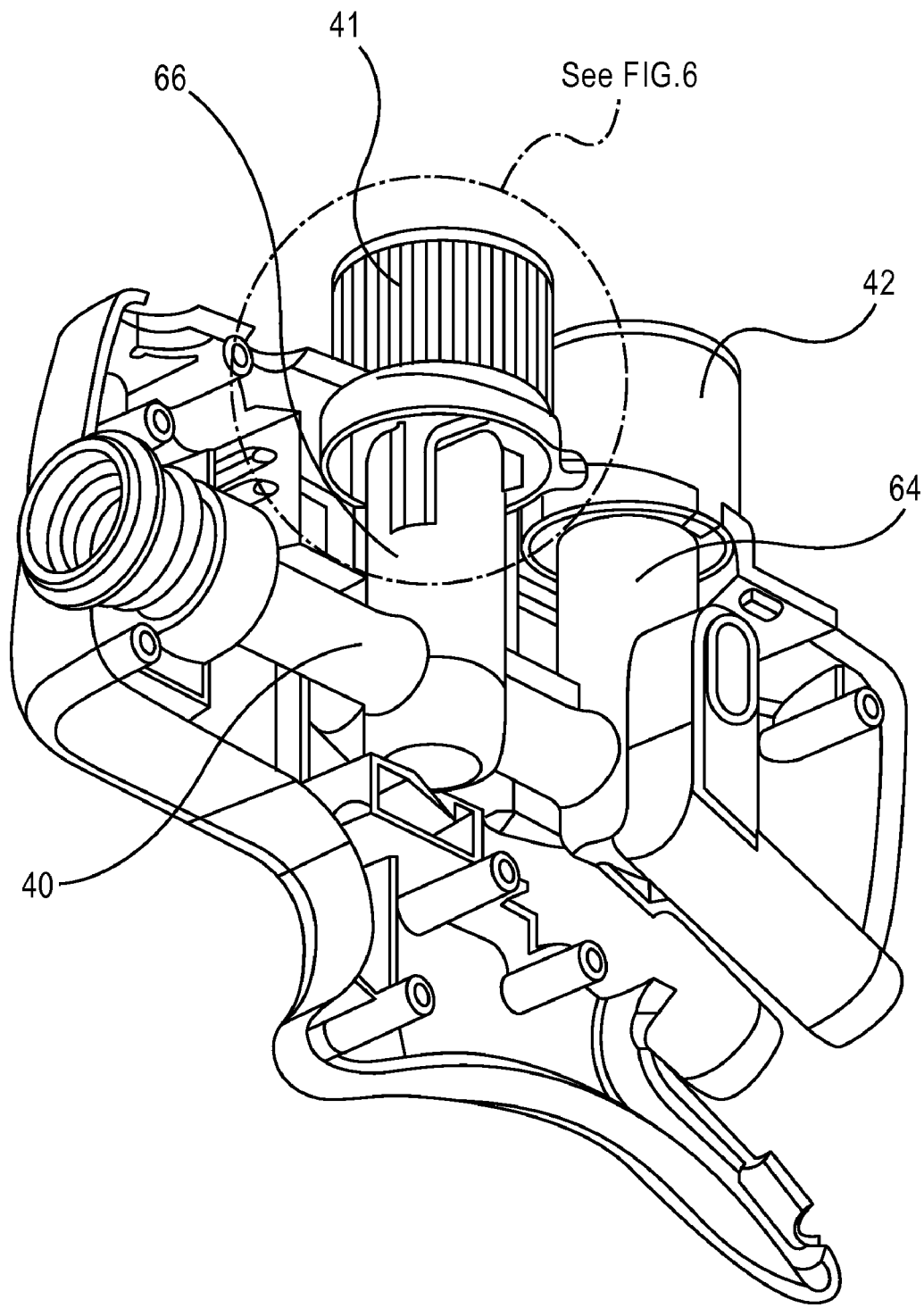
FIG. 5A is a perspective view of one half of a handpiece housing depicting internal components of a medical device located therein, according to an embodiment of the present disclosure.
Figure 5B:
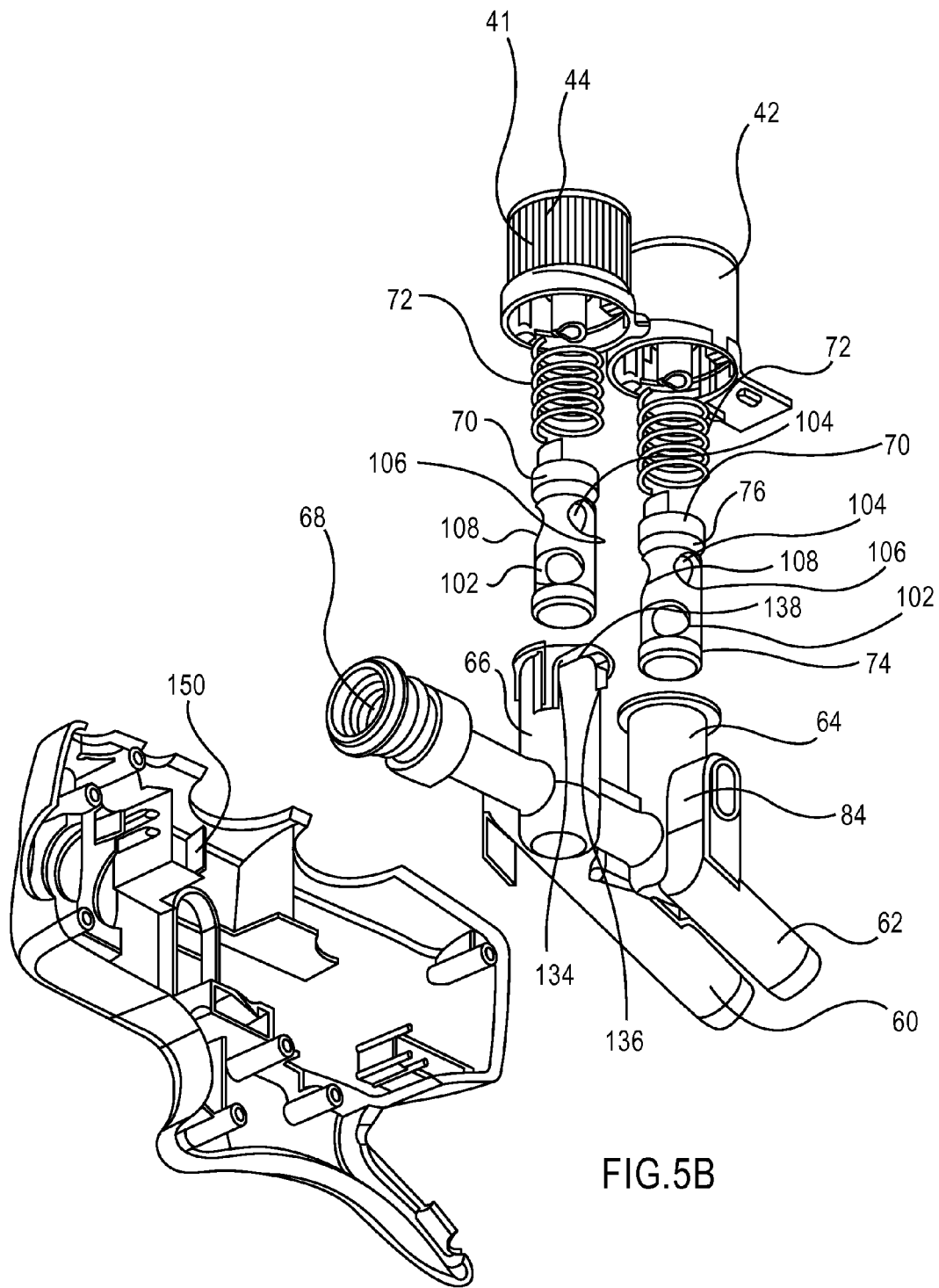
FIG. 5B is a disassembled perspective of the medical device of FIG. 5A, according to an embodiment of the present disclosure.
Figure 6:
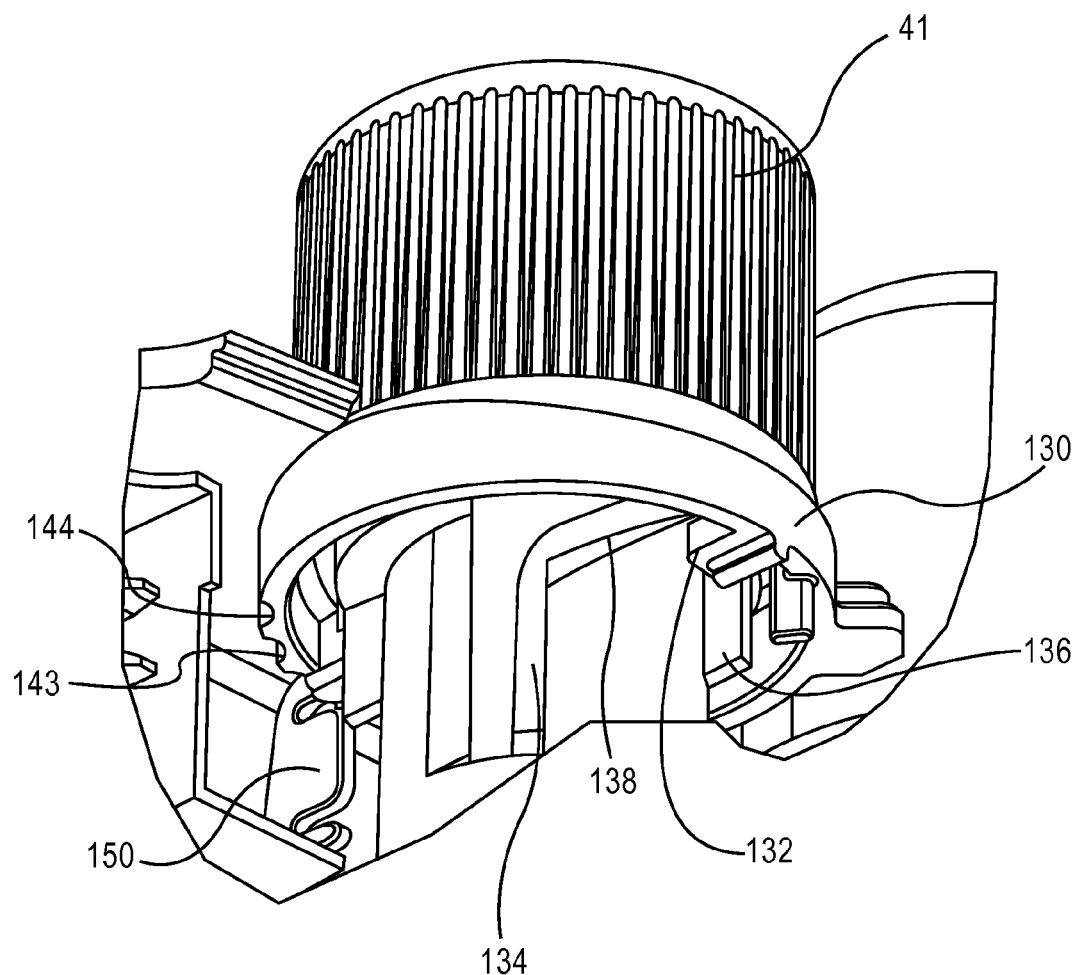
FIG. 6 is an enlarged view of the circled portion of FIG. 5A, according to an embodiment of the present disclosure.

FIG. 5A shows a perspective view of one half of a handpiece housing 11 depicting internal components of a medical device 10. FIG. 6 is an enlarged view of the circled portion of FIG. 5A. FIG. 6 illustrates an embodiment of suction control button 41, that provides a capability for an operator to easily and quickly effectuate an adjustable level of smoke evacuation in addition to full suction.

As noted above, an operator can adjust the magnitude of suction by varying the size of the opening created along the suction flow path 90. This size can be selectively controlled and adjusted as a function of the distance piston 70 is displaced within chamber 66. In the embodiment of FIGS. 6-16, the suction control button 41 is capable of actuating suction through downward displacement as described above. In addition, FIGS. 6-16 describe a system that provides the capability to provide a "fine" adjustment of suction force actuation.

Figure 12:
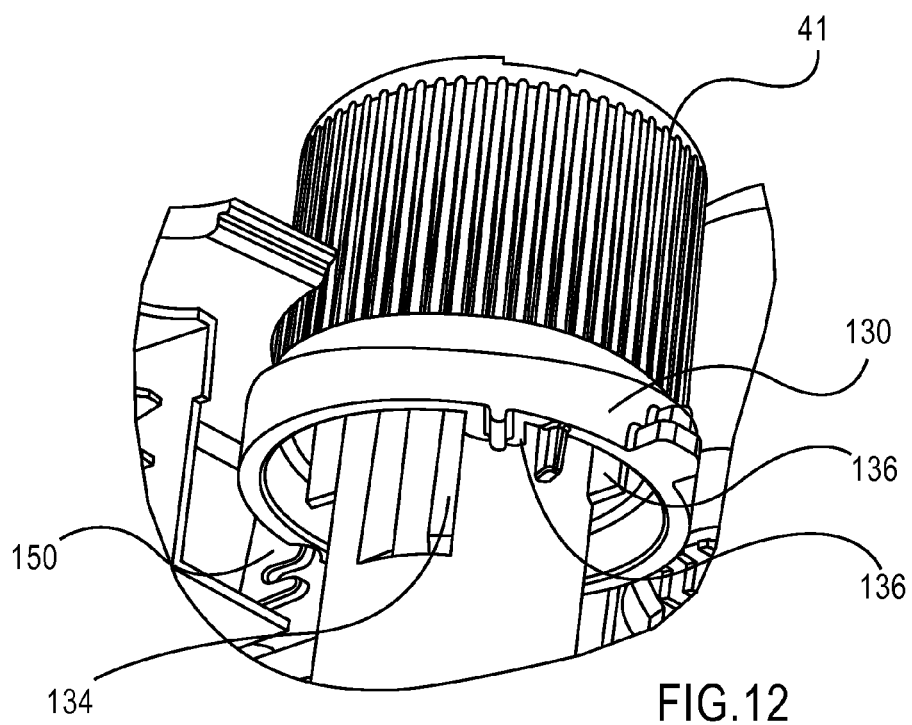
FIG. 12 is an enlarged view of the circled portion of FIG. 11, according to an embodiment of the present disclosure.

The enlarged view of FIG. 6 depicts a suction control button 41 having an expanded annular base portion 130. The base 130 further defines a protrusion 132 extending radially inwardly from base portion 130. As best seen in FIGS. 5B, 6, and 12, the exterior surface of the suction piston valve housing chamber 66 may be provided with a left vertical barrier 134 and a right vertical barrier 136. A downwardly directed ramp 138 extends along an external surface of chamber 66 between the left vertical barrier (or limit) 134 and the right vertical barrier (or limit) 136. As seen in FIG. 6, upon final assembly and in the resting position under the force of compression spring 72, the protrusion 132 of base portion 130 may be located within the area bounded by the ramp 138 and between the left vertical barrier 134 and the right vertical barrier 136.

In this configuration, clockwise rotation of suction control button 41 relative to the suction piston valve housing chamber 66 results in vertical displacement of button 41 (and therefore piston 70 within chamber 66). FIG. 12 depicts the slight vertical displacement of suction control button 41 upon rotation of base portion 130 from a position where protrusion 132 contacts the right vertical barrier 136 at the top of ramp 138 (FIG. 6) to a position where protrusion 132 contacts the left vertical barrier 134 at the base of ramp 138. Due to the sliding contact between protrusion 132 and the underside of ramp 138, clockwise rotation of suction control button 41 results in a vertical displacement of piston 70 within chamber 66 by a distance equal to the vertical distance traversed by ramp 138.

Moreover, rotation of the suction control button 41 also rotates the piston 70 within the suction piston valve housing chamber 66, thereby effecting the resulting alignment between aperture 102 and the distal manifold fluid conduit 68. In other words, the actuation of suction (including smoke evacuation) is brought about by the controlled alignment between aperture 102 of piston 70 and distal manifold fluid conduit 68, by virtue of axial displacement and well as rotational displacement of piston 70 within chamber 66. Accordingly, an operator can selectively actuate a fine vertical and rotational adjustment corresponding to a slight displacement of a piston 70 within chamber 66 to effectuate smoke evacuation simply and quickly during a medical procedure. While the rotational control of suction magnitude is described above with regard to the suction control button 41, it is contemplated that similar structure could be provided for adjusting the magnitude and force of irrigation fluid supplied to the distal manifold fluid conduit 68 by irrigation control button 42.

Figure 7:
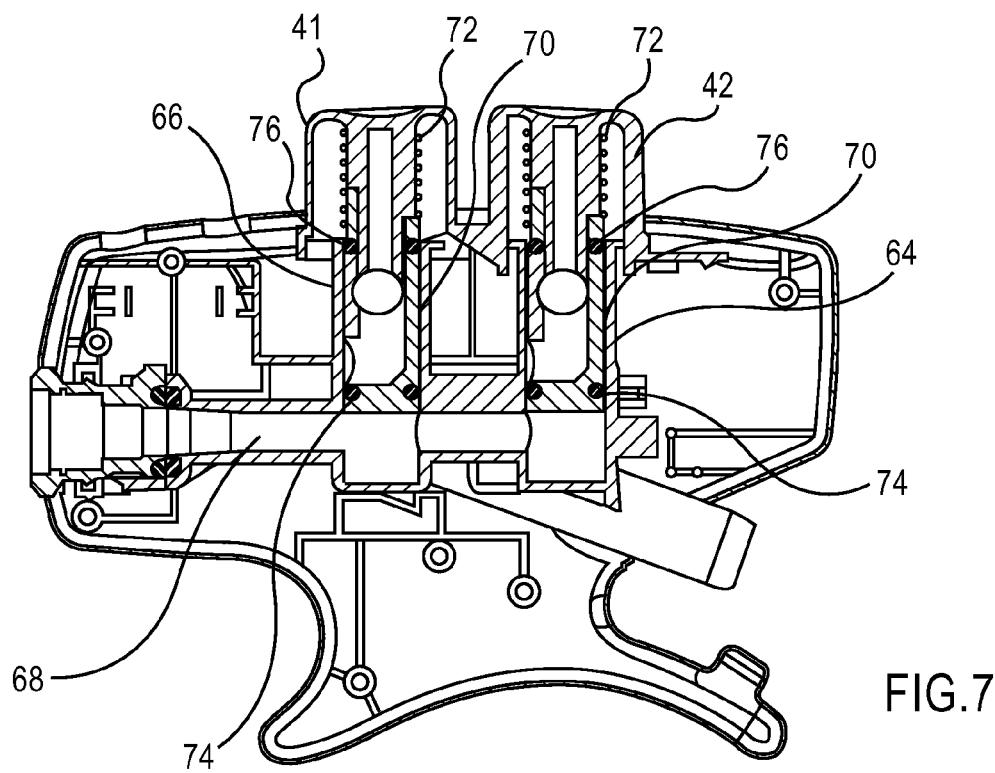
FIG. 7 is a cross-sectional view of the medical device handpiece of FIG. 8 taken along line 7-7 in FIG. 8, according to an embodiment of the present disclosure.
Figure 8:
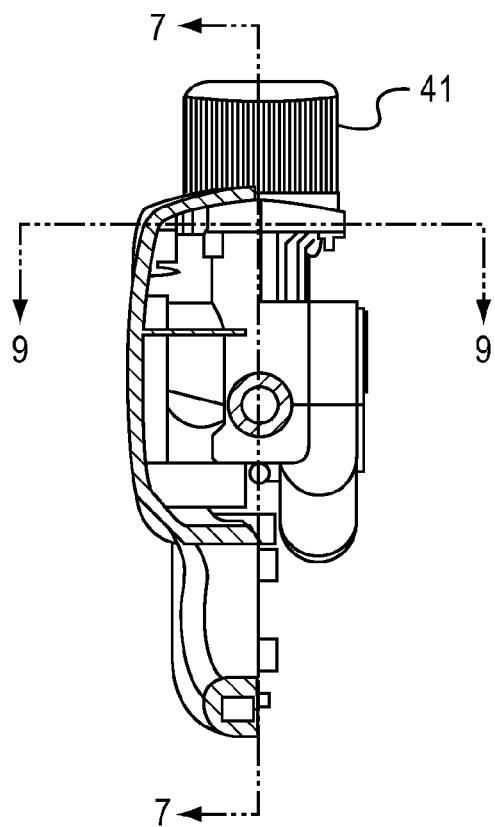
FIG. 8 is a cross-sectional view of the medical device handpiece of FIG. 9 taken along line 8-8 in FIG. 9, according to an embodiment of the present disclosure.
Figure 9:
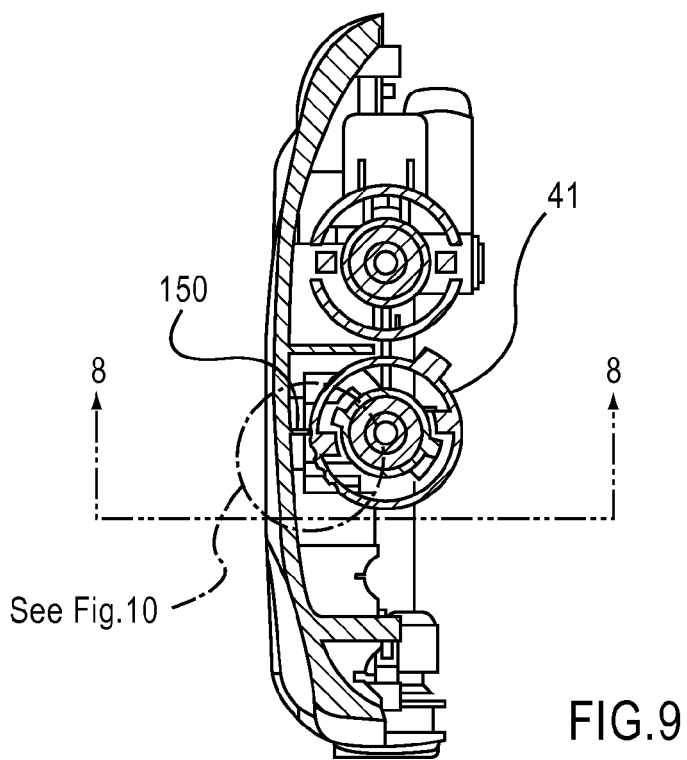
FIG. 9 is a cross-sectional view of the medical device handpiece of FIG. 8 taken along line 9-9 in FIG. 8, according to an embodiment of the present disclosure.

FIGS. 7-9 depict various cross-sectional views of the medical device handpiece 15 in the resting position of FIG. 6 (prior to smoke evacuation). FIG. 7 shows a cross-sectional view of the medical device handpiece of FIG. 8 taken along line 7-7 in FIG. 8. In FIG. 7, suction control button 41 is shown in its upward resting position under the force of spring 72. As shown, the lower "o"-ring seal 74 is not displaced into the distal manifold conduit 68, and therefore, suction flow path 90 remains blocked (also due to the misalignment of aperture 102 and conduit 68). FIG. 9 is a cross-sectional view of the medical device handpiece of FIG. 8, taken along line 9-9 in FIG. 8 and FIG. 10 is an enlarged view of the circled portion of FIG. 9.

Figure 10:
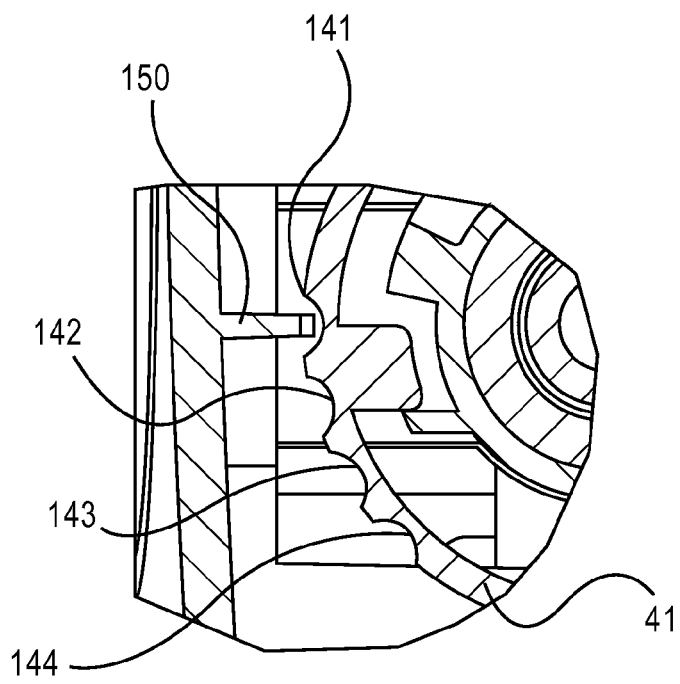
FIG. 10 is an enlarged view of the circled portion of FIG. 9, according to an embodiment of the present disclosure.
Figure 11:
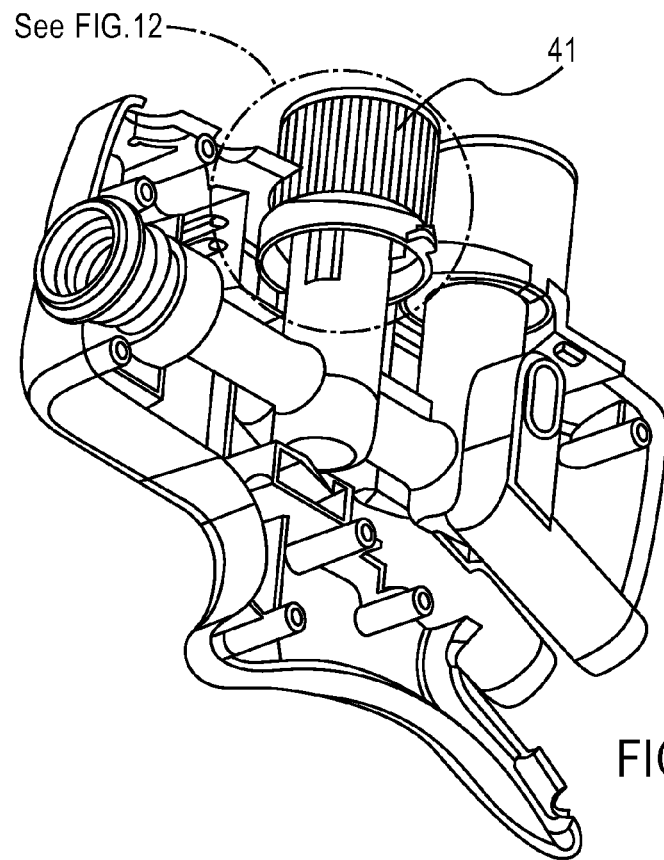
FIG. 11 is a perspective view of one half of a handpiece housing depicting internal components of a medical device located therein and in a suction activated position, according to an embodiment of the present disclosure.

FIG. 10 shows a series of detents or scalloped slots 141, 142, 143, and 144 between about an 8 o'clock and a 9 o'clock position along annular base 130 of suction control button 41. At least detents 143 and 144 are visible in the enlarged perspective view of FIG. 6. As seen in FIGS. 6, 9, and 10, an internal portion of the first (right) housing half 17 includes a vertical spring tab 150. When the suction control button is in the resting position, the vertical spring tab 150 releasably engages the first scalloped slot 141. Upon clockwise rotation of the suction control button 41, the consecutive scalloped slots 142-144 releasably engage with the spring tab 150. Upon engagement of spring tab 150 with the next slot 142-144, a tactile click is felt and heard by the operator.

As button 41 is rotated to the new location, suction control button 41 (and therefore piston 70) can be retained within a particular displacement position providing a particular corresponding magnitude of smoke evacuation force without the continued application of torque upon suction control button 41 by an operator. Accordingly, engagement of spring tab 150 with the first slot 141 equates to a "home" valve closed position, corresponding to no applied suction. Engagement of spring tab 150 with second slot 142 equates to a "low" smoke evacuation position, corresponding to a relatively small suction force applied to the treatment site. Engagement of spring tab 150 with third slot 143 equates to a "medium" smoke evacuation position, corresponding to a slightly greater suction force, and engagement of spring tab 150 with the fourth slot 144 equates to a "high" smoke evacuation position, corresponding to a relatively larger suction force applied to the treatment site. No matter what rotational orientation the suction control button is in (e.g., corresponding to an off, low, intermediate, or high position), there remains the capability to further axially displace suction control button 41 (and therefore piston 70) to activate further suction within the distal manifold conduit 68.

Figure 13:
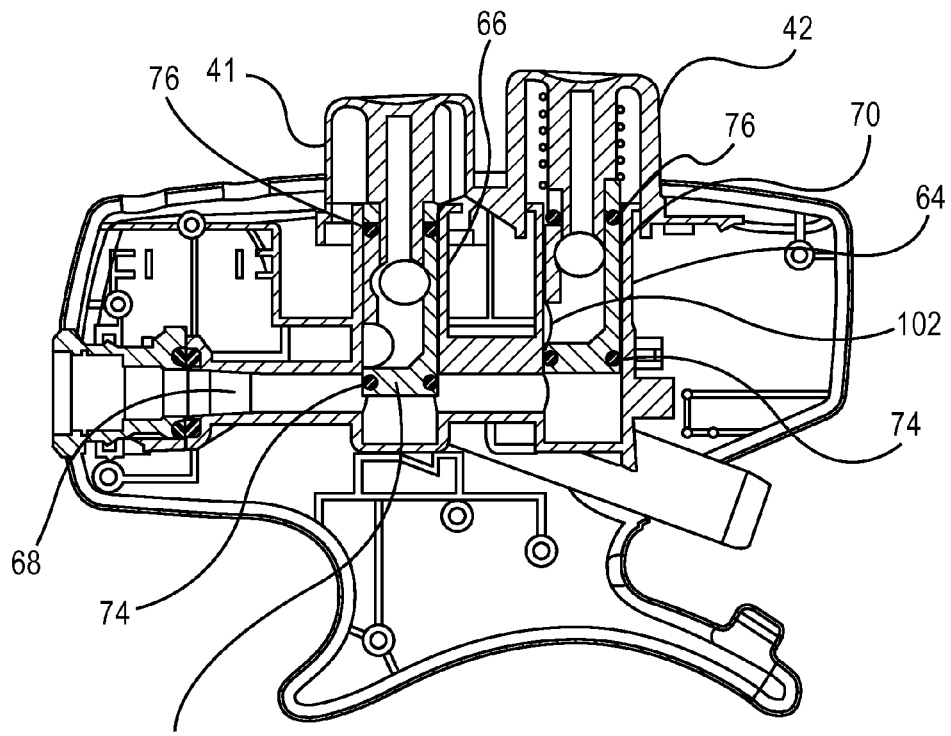
FIG. 13 is a cross-sectional view of the medical device handpiece of FIG. 14 taken along line 13-13 in FIG. 14, according to an embodiment of the present disclosure.
Figure 14:
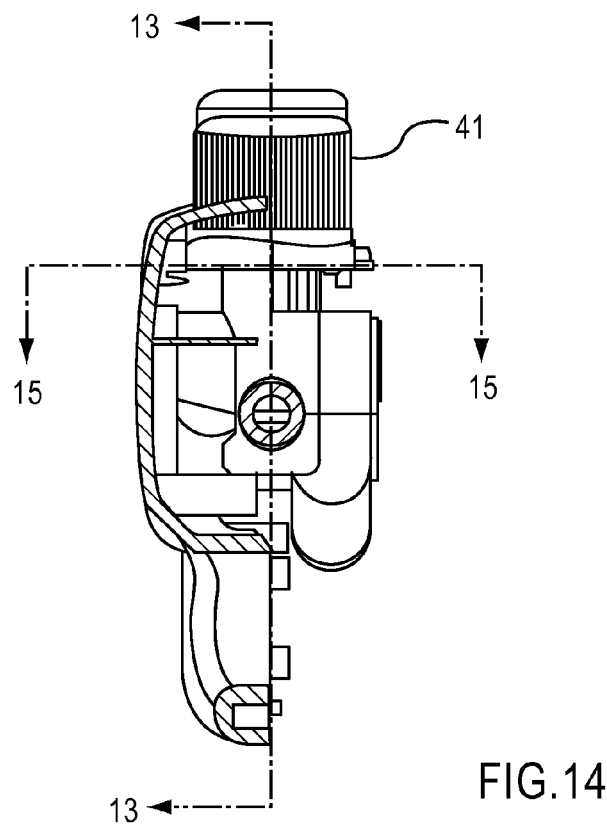
FIG. 14 is a cross-sectional view of the medical device handpiece of FIG. 15 taken along line 14-14 in FIG. 15, according to an embodiment of the present disclosure.
Figure 15:
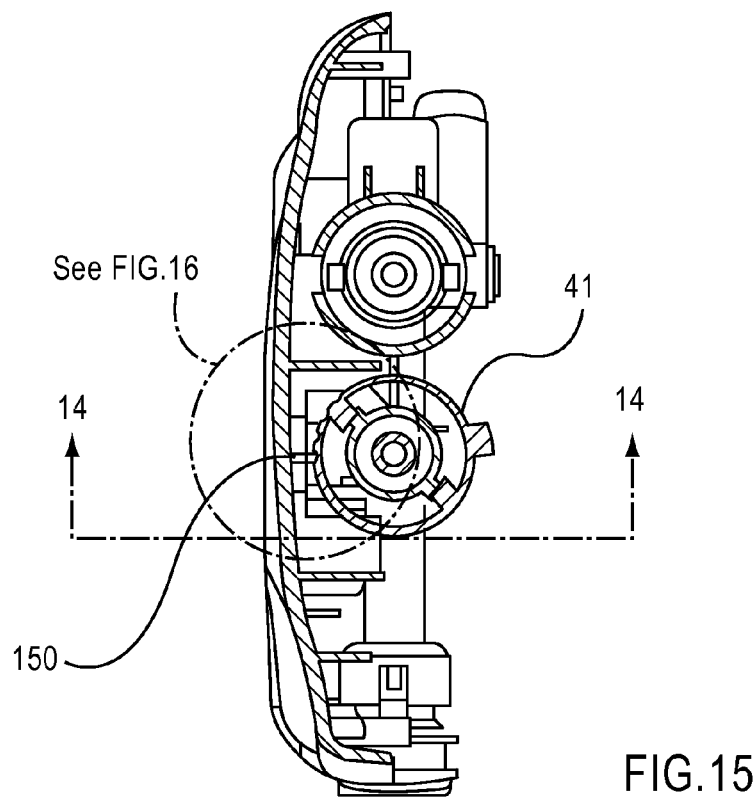
FIG. 15 is a cross-sectional view of the medical device handpiece of FIG. 14 taken along line 15-15 in FIG. 14, according to an embodiment of the present disclosure.
Figure 16:
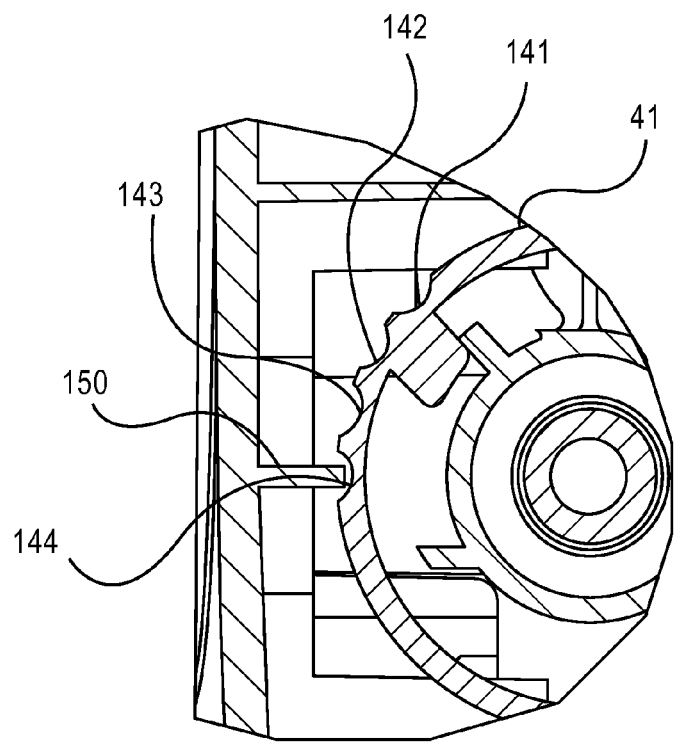
FIG. 16 is an enlarged view of the circled portion of FIG. 15, according to an embodiment of the present disclosure.

FIGS. 13-16 depict various cross-sectional views of the medical device handpiece 15 in the "high" smoke evacuation position of FIG. 12. FIG. 13 shows a cross-sectional view of the medical device handpiece of FIG. 14 taken along line 13-13 in FIG. 14. In FIG. 13, suction control button 41 is shown in its "high" smoke evacuation position where protrusion 132 is in contact with the left barrier 134. As shown, the lower "o"-ring seal 74 is partially displaced within the distal manifold conduit 68 and therefore, suction flow path 90 is no longer blocked. FIG. 15 is a cross-sectional view of the medical device handpiece of FIG. 14 taken along line 15-15 in FIG. 14, and FIG. 16 is an enlarged view of the circled portion of FIG. 15. As seen in FIG. 16, in the high smoke evacuation position, spring tab 150 engages with the fourth slot 144 along the annular base 130 of the suction control button 41.

Figure 25:
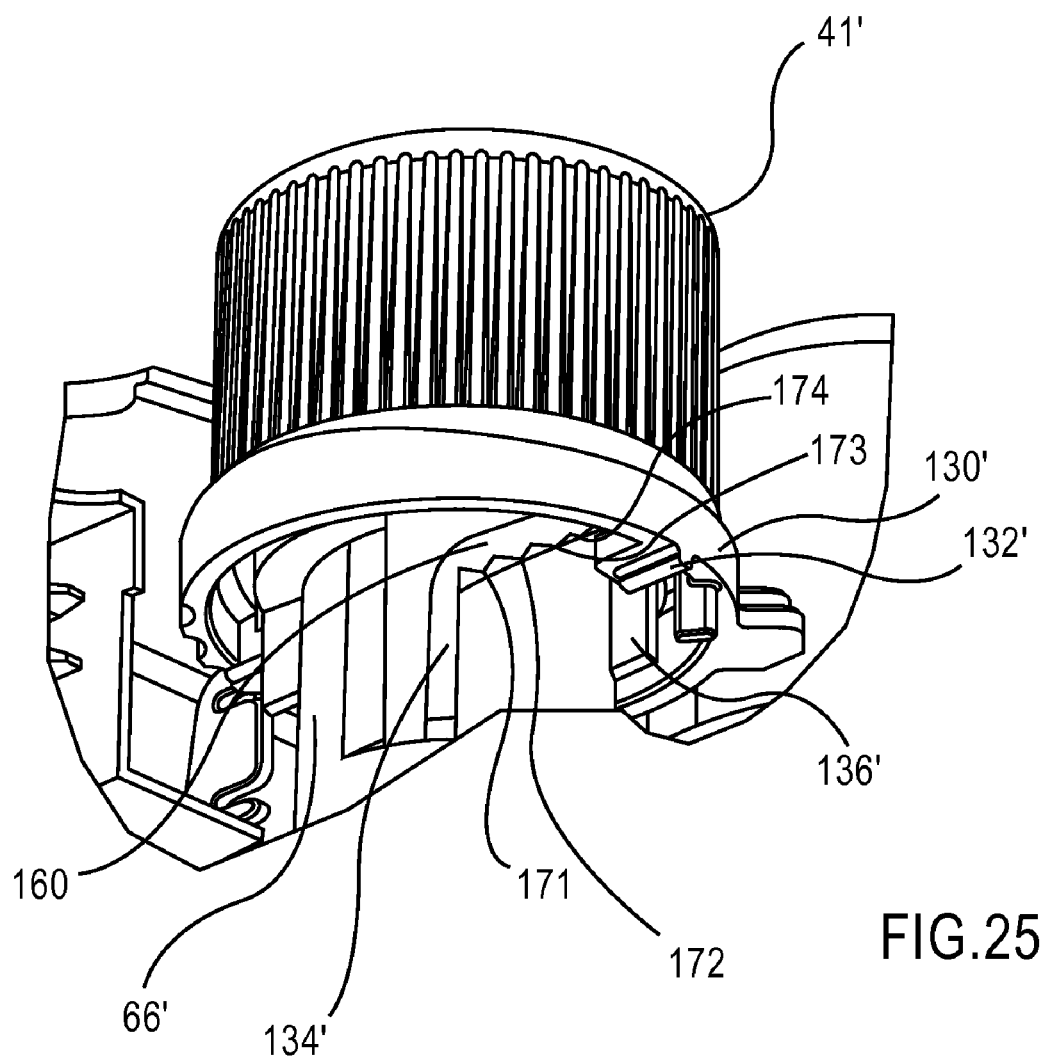
FIG. 25 is an enlarged perspective view of an alternative suction control mechanism in an unactivated position, according to an embodiment of the present disclosure.

FIG. 25 is an enlarged perspective view of an alternative suction control mechanism in an unactivated position. FIG. 25 includes a suction control button 41'. The enlarged view of FIG. 25 depicts a suction control button 41' having an expanded annular base portion 130'. The base 130' further defines a protrusion 132' extending radially inwardly from base portion 130'. The exterior surface of the suction piston valve housing chamber 66' may be provided with a left vertical barrier 134', a right vertical barrier 136', and a ramp 160 extending downwardly along an external surface of chamber 66' from the right vertical barrier 136' to the left vertical barrier 134'. As seen in FIG. 25, upon final assembly and in the resting position under the force of a compression spring 72, the protrusion 132' of base portion 130' may be located within the area bounded by the ramp 160 and between the left vertical barrier 134' and the right vertical barrier 136'. Ramp 160 further includes ratchet detents 171-174. The disclosed number of ratchet detents is exemplary and it is contemplated that a number greater or less than four could be provided.

In this configuration, clockwise rotation of suction control button 41' relative to the suction piston valve housing chamber 66' results in vertical displacement of button 41' (and therefore a piston 70 within chamber 66'). Just as in the above embodiments where spring tab 150 engaged with scalloped slots 141-144, protrusion 132' of base 130' can releasably engage with the ratchet detents 171-174 along ramp 160. Consecutive engagement with each further detent 171-174 can retain the suction control button 141' in a particular position corresponding to a desired level of smoke evacuation.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a housing having a proximal end and a distal end;
   an attachment structure located at the distal end of the housing and which is configured for coupling to a medical instrument;
   at least one of a suction port or an irrigation port located at the proximal end of the housing and which is configured for connection to a source of suction or irrigation, respectively;
   a conduit providing a fluid flow path from the at least one port at the proximal end of the housing to a distal port leading to the medical instrument at the distal end of the housing;
   a valve housing chamber comprising a ramp that extends along an external surface of the valve housing chamber; and
   at least one valve configured to move within the fluid flow path to selectively actuate suction or irrigation, wherein the at least one valve is configured to rotate along a path defined by the ramp of the valve housing chamber to permit a first level of suction or irrigation and is configured to axially displace along a longitudinal axis of the valve housing chamber in a non-rotating manner to permit a second, higher level of suction or irrigation.

2. The medical device of claim 1, wherein the at least one valve is configured for axial displacement regardless of a rotational orientation of the at least one valve.

3. The medical device of claim 1, wherein the at least one valve comprises a piston located within the valve housing chamber, the piston movable between a first position blocking fluid flow along the fluid flow path and a second position allowing fluid flow along the fluid flow path.

4. The medical device of claim 3, wherein the piston is engaged with an actuation button and maintained in the first position through a compression spring positioned between the valve housing chamber and the actuation button.

5. The medical device of claim 3, wherein the conduit defines a lumen along a distal portion thereof, the piston includes at least one aperture, and the piston is in the second position when the aperture is moved to at least partially align the aperture with the lumen.

6. The medical device of claim 5, wherein the piston is engaged with an actuation button and maintained in the first position through a compression spring positioned between the valve housing chamber and the actuation button.

7. The medical device of claim 6, wherein depressing the actuation button compresses the spring and displaces the piston within the valve housing chamber to at least partially align the aperture with the lumen.

8. The medical device of claim 5, wherein the at least one valve is configured to provide an incremental adjustment of a magnitude of applied irrigation or suction.

9. The medical device of claim 8, wherein the incremental adjustment is effectuated by a degree to which the aperture is aligned with the lumen.

10. The medical device of claim 8, wherein axial displacement of the piston within the valve housing chamber controls a degree to which the aperture is aligned with the lumen.

11. The medical device of claim 9, further comprising a spring tab located on the housing and a series of spaced slots connected to the piston, and wherein the spring tab releasably engages each slot to maintain a particular alignment between the aperture and lumen upon movement of the piston.

12. The medical device of claim 1, wherein the at least one valve is configured to provide an incremental adjustment of a magnitude of applied irrigation or suction.

13. The medical device of claim 12, wherein a suction control button extends from the housing, and wherein axial displacement of the suction control button provides the second level of suction, and rotation of the suction control button provides the first level of suction.

14. The medical device of claim 13, wherein the suction control button includes a knurled exterior surface.

15. The medical device of claim 13, further comprising a spring tab located on the housing and a series of spaced slots along an exterior surface of the suction control button, and wherein the spring tab is configured to consecutively releasably engage each slot upon rotation of the control button to engage a particular slot with the tab.

16. The medical device of claim 1, wherein the at least one suction port or an irrigation port is a suction port and an irrigation port provided at the proximal end of the housing, the suction port configured for connection to a source of suction, and the irrigation port configured for connection to a source of irrigation;
a first fluid passageway provides a first fluid flow path from the suction port to the distal port, a second fluid passageway provides a second fluid flow path from the irrigation port to the distal port, the at least one valve comprises a first valve configured to move within the first fluid flow path to selectively actuate suction, wherein the first valve is configured to rotate to permit a first level of suction and is configured to axially displace to permit a second, higher level of suction.

17. The medical device of claim 16, wherein the at least one valve further comprises a second valve configured to move within the second fluid flow path to selectively actuate irrigation, wherein the second valve is configured to axially displace to permit actuation of irrigation.

18. The medical device of claim 17, wherein the first and second valves are configured for axial displacement regardless of a rotational orientation of the valves.

19. The medical device of claim 17, wherein the first and second valves have pistons with substantially identical configurations.

20. The medical device of claim 1, wherein the at least one valve comprises a piston defining a cylinder having a lower distally directed aperture located along an external surface of the cylinder, the piston further including an upper, transverse aperture extending completely through an upper portion of the cylinder.

21. The medical device of claim 20, wherein each cylinder includes a lower "o"-ring seal and an upper "o"-ring seal circumscribing an external surface of the cylinder.

22. The medical device of claim 5, wherein the ramp of the valve housing chamber extends between a first limit and a second limit, and the actuation button includes an inward protrusion that engages the ramp such that rotating the actuation button between the limits causes at least partial alignment between the aperture and the lumen.

23. The medical device of claim 22, wherein the medical device includes electric conductors providing electric current configured to connect to a medical instrument and wherein the first level of suction comprises smoke evacuation.

24. A method for operating a medical device to perform a medical procedure, comprising:
providing a medical device comprising:
a handpiece housing having a proximal end and a distal end;
a medical instrument connected to the distal end of the handpiece housing;
at least one of a suction port or an irrigation port located at the proximal end of the housing and which is configured for connection to a source of suction or irrigation respectively;
a conduit providing a fluid flow path from the at least one port at the proximal end of the housing to a distal port leading to the medical instrument at the distal end of the housing;
a valve housing chamber comprising a ramp that extends along an external surface of the valve housing chamber; and
at least one valve configured to move within the fluid flow path to selectively actuate suction or irrigation, wherein the at least one valve is configured to rotate along a path defined by the ramp of the valve housing chamber to permit a first level of suction or irrigation and is configured to axially displace along a longitudinal axis of the valve housing chamber in a non-rotating manner to permit a second, higher level of suction or irrigation;
connecting at least one of the suction port and the irrigation port to a source of suction or irrigation;
positioning the medical instrument proximate a treatment site; and actuating either irrigation or suction by controlling movement of the valve.

25. The method of claim 24, further comprising incrementally adjusting the magnitude of applied irrigation or suction.

26. The method of claim 25, wherein a suction control button extends from the housing of the medical device, and the method further comprises axially displacing the suction control button to provide suction.

27. The method of claim 26, further comprising rotating the suction control button to provide the first level of suction.

28. The method of claim 27, further comprising rotating the suction control button prior to axially displacing the suction control button.

29. The method of claim 25, wherein an irrigation control button extends from the housing of the medical device, and the method further comprises axially displacing the irrigation control button to provide irrigation.

30. The method of claim 29, further comprising rotating the irrigation control button to adjust a magnitude of applied irrigation.

31. The method of claim 27, further comprising cauterizing tissue with the medical instrument prior to rotating the suction control button.

32. The method of claim 24, wherein providing the medical device further comprises:
  providing a suction port and an irrigation port provided at the proximal end of the housing, the suction port configured for connection to a source of suction, and the irrigation port configured for connection to a source of irrigation;
  providing a first fluid passageway providing a first fluid flow path from the suction port to the distal port, a second fluid passageway providing a second fluid flow path from the irrigation port to the distal port, the at least one valve comprising a first valve configured to move within the first fluid flow path to selectively actuate suction, a second valve configured to move within the second fluid flow path to selectively actuate irrigation, wherein the first valve is configured to rotate to permit a first level of suction and is configured to axially displace to permit a second, higher level of suction; the method further comprising:
  connecting at least one of the suction and irrigation ports to a source of suction or irrigation; and
  actuating both irrigation and suction by controlling movement of the first and second valves.

33. The method of claim 24, wherein the medical device includes structure that releasably engages the at least one valve and the method further comprises maintaining an intermediate level of suction or irrigation by maintaining a particular rotational or axial position of the valve.

34. A medical device, comprising:
  a housing having a proximal end and a distal end;
  an attachment structure located at the distal end of the housing and which is configured for coupling a medical instrument;
  a suction port and an irrigation port provided at the proximal end of the housing, the suction and irrigation ports being configured for connection to a source of suction and irrigation respectively;
  a first fluid passageway providing a first fluid flow path from the suction port at the proximal end of the housing, extending through a suction piston chamber, and out a lumen defined by a distal conduit leading to the medical instrument at the distal end of the housing,
  a second fluid passageway providing a second fluid flow path from the irrigation port at the proximal end of the housing, extending through an irrigation piston chamber, and out the lumen defined by a distal conduit,
  an identical movable piston provided within each of the suction piston chamber and the irrigation piston chamber; and
  a ramp that extends along an external surface of the suction piston chamber, wherein the piston in the suction piston chamber is configured to rotate along a path defined by the ramp of the suction piston chamber and axially translate along a longitudinal axis of the valve housing chamber in a non-rotating manner to provide suction to the medical instrument.

35. The medical device of claim 34, wherein the piston in the suction piston chamber is configured for axial displacement regardless of a rotational orientation of the piston.

36. The medical device of claim 34, wherein each piston defines a cylinder having a lower distally directed aperture located along an external surface of the cylinder, the piston further including an upper, transverse aperture extending completely through an upper portion of the cylinder.

37. The medical device of claim 36, wherein the lower aperture is oriented in substantially perpendicular relation to the axis defined by the upper, transverse aperture.

38. The medical device of claim 37, wherein each cylinder includes a lower "o"-ring seal and an upper "o"-ring seal circumscribing an external surface of the cylinder.

39. The medical device of claim 38, wherein the lower aperture and the upper aperture are both located between the lower and upper "o"-ring seals along the cylinder of the piston.

40. The medical device of claim 34, wherein each piston is engaged with an actuation button and maintained in a first position through a compression spring positioned between the piston chamber and the actuation button.

41. The medical device of claim 40, wherein depressing an actuation button compresses the spring and displaces the piston within the piston chamber to at least partially align an aperture in the piston with the first or second fluid passageway.

42. The medical device of claim 40, further comprising a spring tab located on the housing and a series of spaced slots along an exterior surface of the actuation button that controls suction, and wherein the spring tab is configured to consecutively releasably engage each slot upon rotation of the control button to engage a particular slot with the tab.

43. The medical device of claim 40, wherein the ramp extends between a first limit and a second limit, and the actuation button includes an inward protrusion that engages the ramp such that rotating the actuation button between the limits causes at least partial alignment an aperture in the piston with the first fluid passageway.

44. The medical device of claim 34, wherein the medical device includes electric conductors providing electric current configured to connect to a medical instrument.

* * * * *